United States Patent
Mirkin et al.

(10) Patent No.: US 7,754,907 B2
(45) Date of Patent: Jul. 13, 2010

(54) ALLOSTERICALLY CATALYZED SIGNAL AMPLIFICATION IN CHEMICAL AND BIOLOGICAL SENSING

(75) Inventors: Chad A. Mirkin, Wilmette, IL (US); Nathan C. Gianneschi, San Diego, CA (US); Jungseok Heo, Glenview, IL (US)

(73) Assignee: Northwestern University, Evanston, IL (US)

( * ) Notice: Subject to any disclaimer, the term of this patent is extended or adjusted under 35 U.S.C. 154(b) by 547 days.

(21) Appl. No.: 11/658,606

(22) PCT Filed: Aug. 18, 2005

(86) PCT No.: PCT/US2005/029787
§ 371 (c)(1),
(2), (4) Date: Jan. 25, 2007

(87) PCT Pub. No.: WO2007/018549
PCT Pub. Date: Feb. 15, 2007

(65) Prior Publication Data
US 2008/0213916 A1   Sep. 4, 2008

Related U.S. Application Data

(60) Provisional application No. 60/602,814, filed on Aug. 18, 2004, provisional application No. 60/652,404, filed on Feb. 10, 2005.

(51) Int. Cl.
*C07F 19/00* (2006.01)
*C07F 9/28* (2006.01)
*G01N 33/53* (2006.01)

(52) U.S. Cl. .............................. 556/14; 556/19; 534/15; 436/501

(58) Field of Classification Search .................. 556/14, 556/19; 534/15; 436/501
See application file for complete search history.

(56) References Cited

OTHER PUBLICATIONS

Benesi and Hildebrand, "A Spectrophotometric Investigation of the Interaction of Iodine with Aromatic Hydrocarbons", J. Am. Chem. Soc., 71:2703-2707 (1949).

Campbell et al., "Unsymmetrical salen-type ligands: high yield synthesis of salen-type Schiff bases containing two different benzaldehyde moieties", Tetrahedron Lett., 42:1221-1225 (2001).

Dixon et al., "Neutral Macrocycles via Halide-Induced Ring Opening of Binuclear Condensed Intermediates", Inorg. Chem., 39:3432-3433 (2000).

Eisenberg et al., "Binuclear Palladium Macrocycles Synthesized via the Weak-Link Approach", Organometallics, 20:2052-2058 (2001).

Evans et al., "Bis(oxazoline) copper (II) Complexes as Chiral Catalysts for the Enantioselective Diels-Alder Reaction", J. Am. Chem. Soc., 115:6460-6461 (1993).

Evans et al., "Bis(imine)-Copper(II) Complexes as Chiral Lewis Acid Catalysts for the Diels-Alder Reaction", Tetrahedron Lett., 34:7027-7030 (1993).

(Continued)

*Primary Examiner*—Porfirio Nazario Gonzalez
(74) *Attorney, Agent, or Firm*—Marshall, Gerstein & Borun LLP

(57) ABSTRACT

Coordination complexes having at least two structural conformations are disclosed. The coordination complexes contain at least one metal center and at least one hemi-labile ligand, and change structural conformations due to the presence or absence of allosteric effectors. Methods of detecting an analyte using the coordination complexes are also disclosed.

25 Claims, 4 Drawing Sheets

OTHER PUBLICATIONS

Farrell et al., "The Weak-Link Approach to the Synthesis of Inorganic Macrocycles", Angew. Chem. Int. Ed., 37:465-467 (1998).

Farrell et al., "Templated Formation of Binuclear Macrocycles via Hemilabile Ligands", Organometallics, 18:4856-4868 (1999).

Gianneschi et al., "Reversibly Addressing an Allosteric Catalyst In Situ: Catalytic Molecular Tweezers", Angew. Chem. Int. Ed., 43:5503-5507 (2004).

Gianneschi et al., "A Supramolecular Approach to an Allosteric Catalyst", J. Am. Chem. Soc., 125:10508-10509 (2003).

Holliday et al., "Metal-Directed Assembly of Triple-Layered Fluorescent Metallocyclophanes", J. Am. Chem. Soc., 121:6316-6317 (1999).

Hu et al., "Chiral Porous Hybrid Solids for Practical Heterogeneous Asymmetric Hydrogenation of Aromatic Ketones", J. Am. Chem. Soc., 125:11490-11491 (2003).

Hua et al., "Chiral Metallacyclophanes: Self-Assembly, Characterization, and Application in Asymmetric Catalysis", Org. Lett., 6:861-864 (2004).

Hug et al., "Investigation of Chiroptical Properties of Helical Copolymers with Aromatic Side Chains", J. Am. Chem. Soc., 96:3407-3410 (1974).

James et al., "Chiral discrimination of monosaccharides using a fluorescent molecular sensor", Nature, 374:345-347 (1995).

Kobe et al., "Active site-directed protein regulation", Nature, 402:373-376 (1999).

Kovbasyuk et al., "Allosteric Supramolecular Receptors and Catalysts" Chem. Rev., 104:3161-3187 (2004).

Kubo et al., "Colorimetric chiral recognition by a molecular sensor", Nature, 382:522-524 (1996).

Lee et al., "The First Chiral Organometallic Triangle for Asymmetric Catalysis", J. Am. Chem. Soc., 124:12948-12949 (2002).

Lee et al., "A Chiral Molecular Square with Metallo-Corners for Enantioselective Sensing", J. Am. Chem. Soc., 124:4554-4555 (2002).

Li et al., "Asymmetric Alkene Aziridination with Readily Available Chiral Diimine-Based Catalysts", J. Am. Chem. Soc., 115:5326-5327 (1993).

Lim et al., "The modular logic of signaling proteins: building allosteric switches from simple binding domains", Curr. Opin. Struct. Biol., 12:61-68 (2002).

Lin et al., "A Practical Enantioselective Fluorescent Sensor for Mandelic Acid", J. Am. Chem. Soc., 124:2088-2089 (2002).

Lin et al., "Bisbinaphthyl Macrocycle-Based Highly Enantioselective Fluorescent Sensors for α-Hydroxycarboxylic Acids", Org. Lett., 4:3297-3300 (2002).

Liu et al., "Flexible Redox-Active Binuclear Macrocycles Formed via the Weak-Link Approach and Novel Hemilabile Ligands with N,N,N',N'-Tetramethyl-1,4-phenylenediamine Units", Inorg. Chem., 40:2940-2941 (2001).

Masar et al., "Binuclear Copper(I) Macrocycles Synthesized via the Weak-Link Approach", Inorg. Chem., 43:4693-4701 (2004).

Mikami et al., "Asymmetric Glyoxylate-Ene Reaction Catalyzed by Chiral Titanium Complexes: A Practical Access to α—hydroxy Esters in High Enantiomeric Purities", J. Am. Chem. Soc., 111:1940-1941 (1989).

Miyashita et al., "Synthesis of 2,2'-Bis(diphenylphosphino)-1,1'-binaphthyl(BINAP), an Atropisomeric Chiral Bis(triaryl)phosphine, and Its Use in the Rhodium(I)-Catalyzed Asymmetric Hydrogenation of α—(Acylamino)acrylic Acids", J. Am. Chem. Soc., 102:7932-7934 (1980).

Nabeshima et al., "Artificial Allosteric Ionophores: Regulation of Ion Recognition of Polyethers Bearing Bipyridine Moieties by Copper (I)", Inorg. Chem., 32:1407-1416 (1993).

Nabeshima et al., "Remarkably Large Positive and Negative Allosteric Effects on Ion Recognition by the Formation of a Novel Helical Pseudocryptand", J. Am. Chem. Soc., 125:28-29 (2003).

Naruta et al., "Catalytic and Asymmetric Epoxidation of Olefins with Iron Complexes of "Twin-Coronet" Porphyrins. A Mechanistic Insight into the Chiral Induction of Styrene Derivatives", J. Am. Chem. Soc., 113:6865-6872 (1991).

Ovchinikov et al., "Threefold symmetric trimetallic macrocycles formed via the Weak-link Approach", Proc. Nat'l. Acad. Sci. USA, 99:4927-4931 (2002).

Peacock et al., "Host-Guest Complexation. 22. Reciprocal Chiral Recognition between Amino Acids and Dilocular Systems", J. Am. Chem. Soc., 102:2043-2052 (1980).

Pescitelli et al., "Multiple Solution Species of Titanium (IV) 1,1'-Bi-2-naphtholate Elucidated by NMR and CD Spectroscopy", Organometallics, 23:4223-4229 (2004).

Pu et al., "Fluorescence of Organic Molecules in Chiral Recognition", Chem. Rev., 104:1687-1716 (2004).

Resendiz et al., "A Self-Assembled Supramolecular Optical Sensor for Ni(II), Cd(II), and Cr(III)", Org. Lett., 6:651-653 (2004).

Rosini et al., "Enantiopure Dendrimers Derived from the 1,1'-Binaphthyl Moiety: A Correlation Between Chiroptical Properties and Conformation of the 1,1'-Binaphthyl Template", Eur. J. Org. Chem., 61-71 (2000).

Saghatelian et al., "DNA Detection and Signal Amplification via an Engineered Allosteric Enzyme", J. Am. Chem. Soc., 125:344-345 (2003).

Xu et al., "Fluorescent Sensors for the Enantioselective Recognition of Mandelic Acid: Signal Amplification by Dendritic Branching", J. Am. Chem. Soc., 124:14239-14246 (2002).

Yoshizawa et al., "And/Or Bimolecular Recognition", J. Am. Chem. Soc., 126:6846-6847 (2004).

Zhang et al., "Biaryl-Based Macrocyclic and Polymeric Chiral (Salophen) Ni(II) Complexes: Synthesis and Spectroscopic Study", J. Org. Chem., 66:481-487 (2001).

Slone et al., in Prog. Inorg. Chem., 48:233, Karlin, K.D., ed., John Wiley & Sons, Inc.: New York (1999).

ALLOSTERICALLY CATALYZED SIGNAL AMPLIFICATION IN CHEMICAL AND BIOLOGICAL SENSING

CROSS-REFERENCE TO RELATED APPLICATIONS

This application claims the benefit of U.S. Provisional Application Ser. No. 60/602,814, filed Aug. 18, 2004, and U.S. Provisional Application Ser. No. 60/652,404, filed Feb. 10, 2005.

STATEMENT OF GOVERNMENTAL INTERESTS

This invention was made with government support under National Science Foundation grant EEC 0118025 and Air Force Office of Scientific Research grant F49620-00-1-0283.

FIELD OF THE INVENTION

The present invention relates to coordination complexes and methods of detecting an analyte using the coordination complexes. In particular, the present invention relates to novel coordination complexes comprising metals and hemi-labile ligands which, upon coordination with an analyte or an allosteric effector, rearrange their coordination environment at the metal and cause a structural conformation change throughout the coordination complex. These structural changes activate the coordination complex for use as a catalyst or for the binding of an analyte. The subsequent catalytic reaction or analyte binding event amplifies the signal and allows for detection of the analyte.

BACKGROUND OF THE INVENTION

Allosteric regulation is a powerful tool utilized efficiently and elegantly in biological systems to control substrate binding and catalysis (Lim et al., *Curr. Opin. Struct. Biol.*, 12:61 (2002); Kobe et al., *Nature*, 402:373 (1999)). Recently, advances have been made in the design of abiotic supramolecular structures that exhibit allosteric or pseudoallosteric behavior analogous to their biological counterparts. Sensors capable of signal amplification (Kovbasyuk et al., *Chem. Rev.*, 104:3161 (2004); Saghatelian et al., *J. Am. Chem. Soc.*, 125:344 (2003); Gianneschi et al., *J. Am. Chem. Soc.*, 125: 10508 (2003); Gianneschi et al., *Angew. Chem. Int. Ed.*, 43:5503 (2004); Nabeshima et al., *J. Am. Chem. Soc.*, 125:28 (2003); Nabeshima et al., *Inorg. Chem.*, 32:1407 (1993); Reaendiz et al., *Org. Lett.*, 6:651 (2004); Yoshizawa, et al., *J. Am. Chem. Soc.*, 126:6846 (2004)) and asymmetric catalysts with activities and enantioselectivities that can be controlled with allosteric regulators have been designed (Gianneschi et al., *J. Am. Chem. Soc.*, 125:10508 (2003); Gianneschi et al., *Angew. Chem. Int. Ed.*, 43:5503 (2004)). Thus far, recognition of analytes induced by an allosteric regulator has not been demonstrated. This capability, however, would be a first step towards a system having recognition properties that could be selectively activated or deactivated using small molecule coordination chemistry at an allosteric regulatory site. Thus, the detection of an analyte of interest either through the allosteric effect of a second molecule on a coordination complex or through the allosteric effect that the analyte has on a coordination complex has not been achieved. Further, the use of these coordination complexes as catalysts with the ability to be activated or deactivated has not been demonstrated.

An analyte of interest can be detected by its ability to alter the coordination about a metal center of a coordination complex in a manner that affects the catalytic activity of the metal center. Alternatively, an analyte of interest can be detected through its ability to coordinate to the coordination complex only in one structural conformation of the coordination complex, wherein the structural conformation for binding the analyte is achieved through first binding an allosteric effector to a coordination complex. Further, the catalytic activity of a catalyst can be modulated by interaction between the catalyst and an allosteric effector.

The presence of the analyte can be detected by different methods, depending upon which of the two processes is in effect. In cases wherein the binding of the analyte activates the catalytic activity of the coordination complex, a product of the catalytic reaction can be detected. In cases wherein the binding of an allosteric effector causes a structural conformation change to the coordination complex, the analyte binds to the new structural conformation of the coordination complex and can be detected. This detection can be achieved through, for example, the addition of a fluorescent detection molecule that acts as a sensor for the binding of the analyte to the coordination complex.

SUMMARY

The present invention relates to coordination complexes. In particular, the present invention provides coordination complexes comprising one or more metal centers and at least one hemi-labile ligand, wherein the coordination complex has at least two structural conformations, e.g., one in which the hemi-labile ligand is fully coordinated to a metal center and one in which the hemi-labile ligand is partially displaced by a second ligand and is semi-coordinated to the metal center. In some embodiments, the coordination complex is arranged in a macrocycle. In other embodiments, the coordination complex assumes a nominally U-shaped conformation, termed herein a tweezer conformation, in which the arms of the tweezer may be spaced in close proximity to one another or spaced apart. The spacing of the arms of the tweezer of the coordination complex can either enable the catalytic ability of the coordination complex or occlude the catalytic activity.

One aspect of the present invention provides coordination complexes that can act as a catalyst, wherein the catalytic ability of the coordination complex is modulated by an allosteric effector.

In another aspect, the invention provides coordination complexes wherein the second ligand is an analyte or an allosteric effector.

Yet another aspect of the present invention provides coordination complexes wherein the coordination complex is chiral and preferentially interacts with a chiral analyte of interest or a chiral allosteric effector.

Still another aspect of the present invention provides coordination complexes wherein the coordination complex is able to catalyze a catalytic reaction, wherein the catalytic ability of the coordination complex is influenced by an allosteric effector.

Another aspect of the invention is to provide a method of detecting an analyte whereby a coordination complex undergoes a structural conformation change upon de-coordination of the labile portion of the hemi-labile ligand and coordination of that site to an allosteric effector. The structural change permits binding of the analyte to the coordination complex.

Still another aspect of the present invention is to provide a method of detecting an analyte wherein a coordination complex undergoes a structural change upon binding to an analyte, which activates the coordination site as an active catalyst. Detection of the analyte occurs indirectly through detection of a product of a subsequent catalytic reaction.

DETAILED DESCRIPTION OF THE PREFERRED EMBODIMENTS

Figure 1:
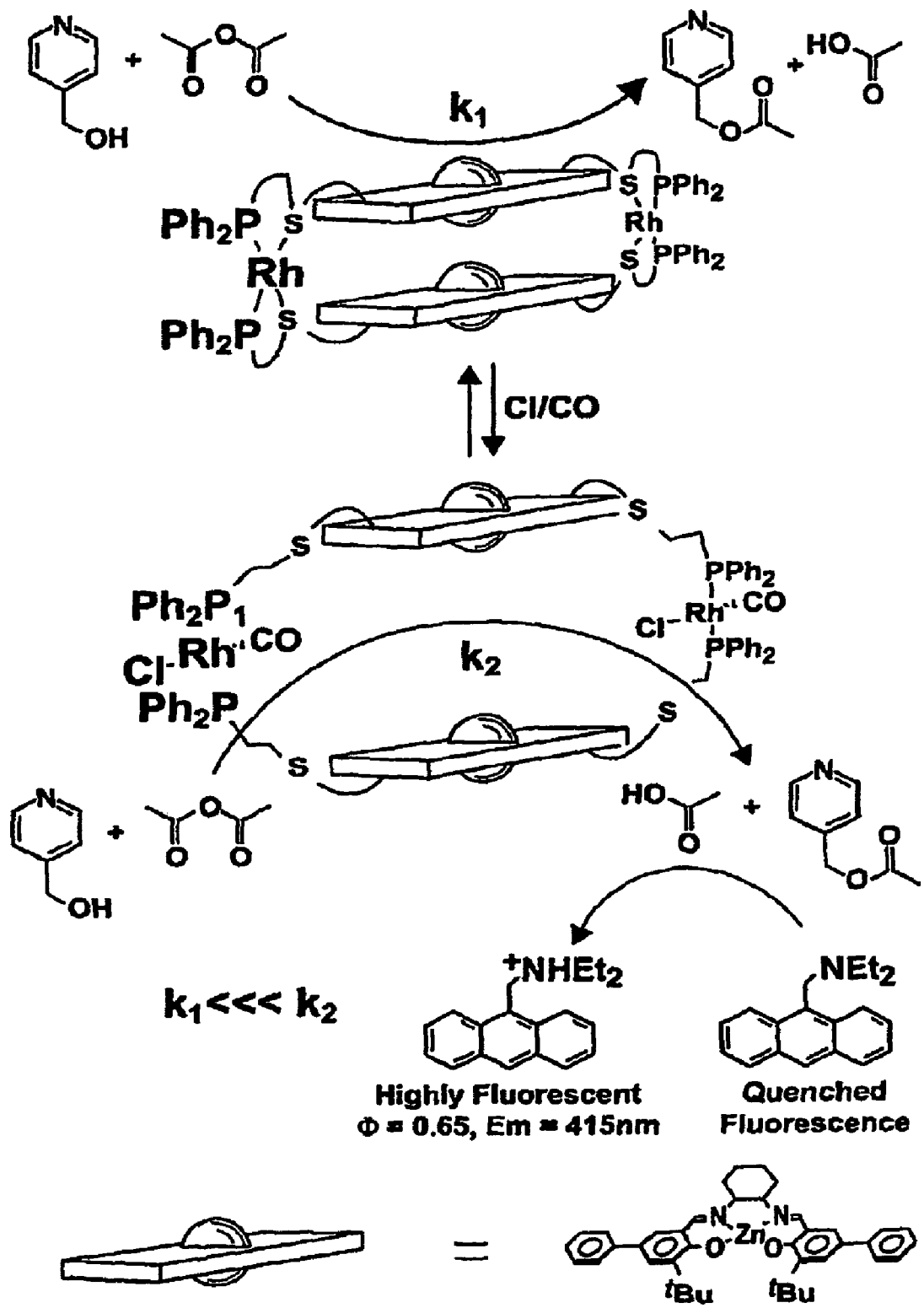
FIG. 1 shows a schematic of a macrocyclic coordination complex that is activated as a catalyst upon binding of an allosteric effector.

A new approach in supramolecular chemistry, termed the Weak Link Approach (WLA), has recently been developed (Farrell et al., *Angew. Chem. Int. Ed.*, 37:465 (1998); Holliday et al., *J. Am. Chem. Soc.*, 121:6316 (1999); Ovchinikov et al., *Proc. Natl. Acad. Sci. USA*, 99:4927 (2002); Farrell et al., *Organometallics*, 18:4856 (1999); Eisenberg et al., *Organometallics*, 20:2052 (2001); Liu et al., *Inorg. Chem.*, 40:2940 (2001); Slone et al., in *Prog. Inorg. Chem.*, 48:233, Karlin, K. D., ed., John Wiley & Sons, Inc.: New York (1999), Dixon, et al., *Inorg. Chem.*, 39:3432 (2000); Masar et al., *Inorg. Chem.*, 43:4693 (2004)). WLA utilizes condensed intermediates templated by hemi-labile ligands that strategically form both strong and weak coordination bonds with metal centers. Such structures can be selectively, and often reversibly, opened into flexible conformations or macrocycles by reacting them with small molecules that break the weak coordination bonds of the hemi-labile ligands to a metal center. This ability to use small molecules to interconvert rigid condensed structures to flexible open conformations or macrocycles is ideal for creating allosterically regulated systems. One embodiment of the present invention utilizes this mediated conformational change to provide catalysts whose activity can be modulated or controlled by allosteric effectors.

A significant advance would be the development of allosteric coordination complexes with chiral recognition elements that could be activated and deactivated. Such a capability would allow the development of (a) receptors and chemical sensors and (b) separation materials that could selectively recognize, transport, manipulate, and chemically release target chiral agents. The present invention utilizes WLA to synthesize coordination complexes comprising a metal and a hemi-labile ligand. For example, a four coordinate copper (I) (Cu(I)) complex in the following scheme having chiral recognition for mandelic acid is activated by chelating 2,2'-bipyridine (bipy) to the Cu(I) center in a reaction that concomitantly breaks weak Cu-sulfur (S) links and opens the condensed structure into a 27 membered macrocycle.

As used herein, "coordination complex" refers to a structure comprising at least one metal center and at least one hemi-labile ligand, and optionally non-labile ligands, labile ligands, or both, wherein the coordination complex has at least two structural conformations related to a complete or partial coordination of the hemi-labile ligand to the metal center, and wherein the two structural conformations exhibit an opposite binding ability to an analyte or allosteric effector, or wherein the structural conformations exhibit differing catalytic activities. The coordination complex can exist as a macrocyclic coordination complex or as a tweezer.

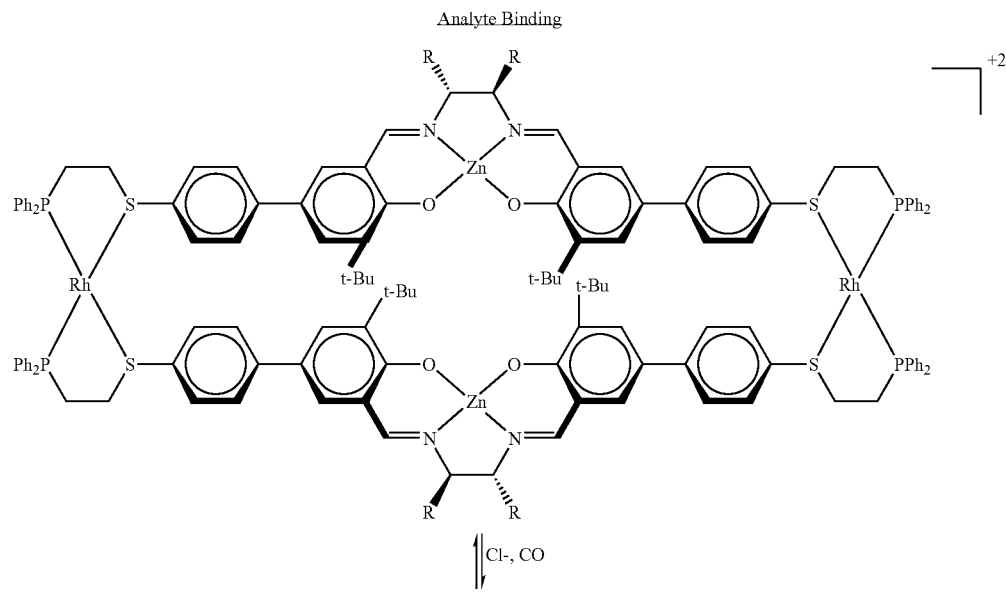

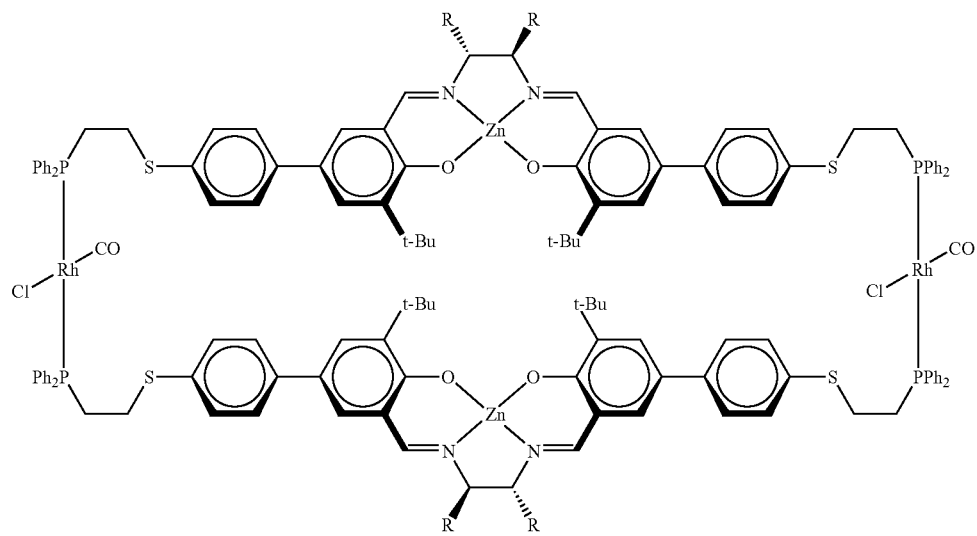

As used herein, a macrocycle is a structure wherein twelve or more atoms are arranged in a continuous ring. Preferred macrocycles of the present invention include 15 to 60 atoms, inclusive. Macrocycles larger than 60 atoms are envisioned, but are not preferred.

As used herein, a tweezer coordination complex is a structural conformation wherein the members of the coordination complex are oriented in a fixed U-shaped manner, as illustrated in the following structure 2, where M can be any metal.

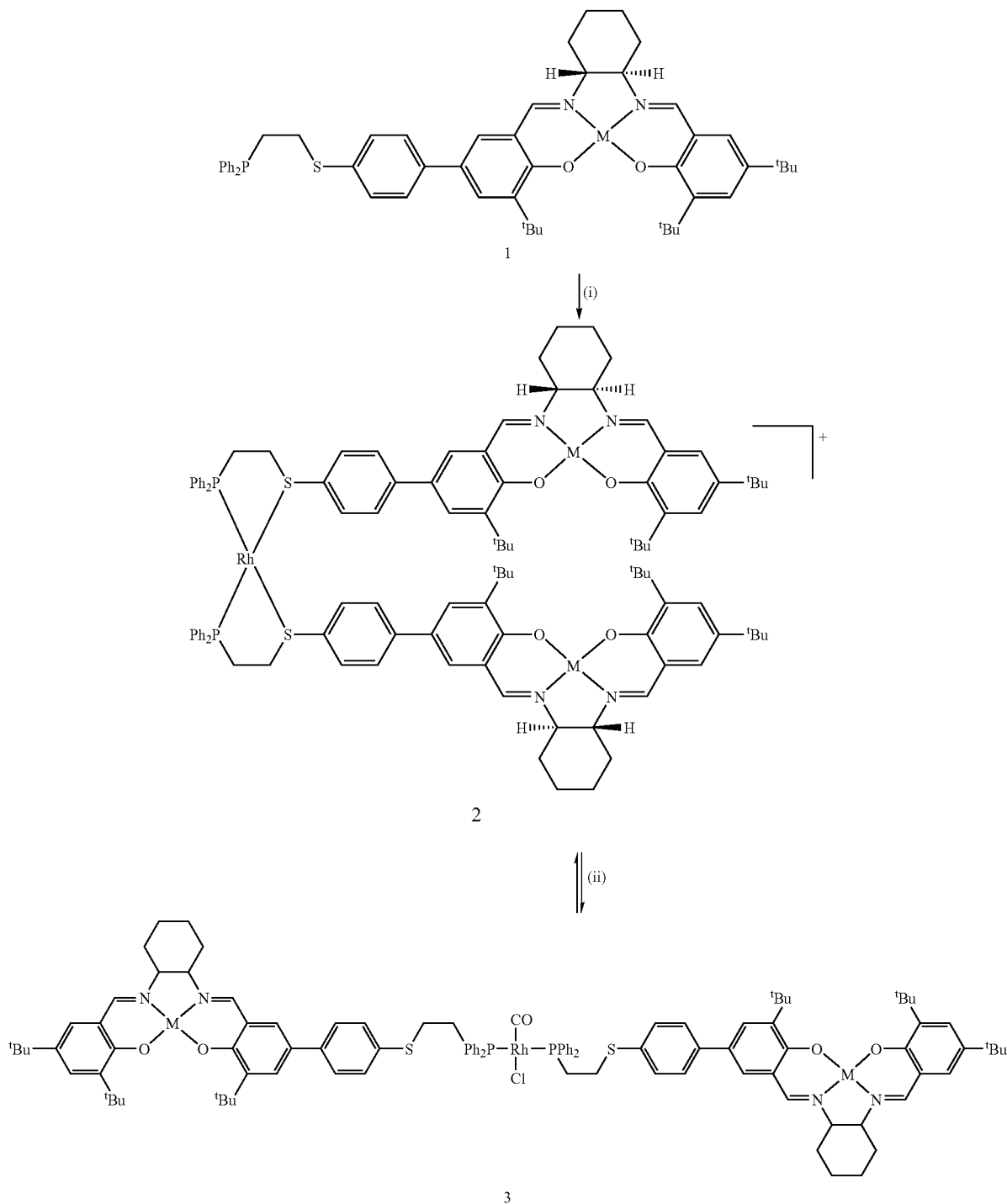

As used herein, "structural conformation" refers to the three-dimensional arrangement of the coordination complex with respect to its metal center(s), hemi-labile ligand(s), and other optional fully labile and non-labile ligands. For example, one structural conformation exists when the hemi-labile ligand is fully complexed to the metal center, while a second structural conformation exists when the hemi-labile ligand is only partially complexed to the metal center.

As used herein, a metal center refers to a metal that is capable of coordinating with various organic and inorganic ligands. Exemplary metals include, but are not limited to, copper, zinc, nickel, cobalt, manganese, chromium, vanadium, titanium, scandium, yttrium, zirconium, niobium, molybdenum, technetium, ruthenium, rhodium, palladium, silver, cadmium, lanthanum, hafnium, tantalum, tungsten, rhenium, osmium, iridium, platinum, gold, tin, cerium, aluminum, magnesium, calcium, strontium, barium, praseodymium, neodymium, promethium, samarium, europium, gadolinium, terbium, dysprosium, holmium, erbium, thulium, ytterbium, lutetium or a mixture thereof. The metal center can be in any oxidation state (e.g., copper (I), copper (II), manganese (III), manganese (V)) and can have any number of ligands coordinated in any coordination geometry (e.g., tetrahedral, square-planar, trigonal bipyramidal, square pyramidal, octahedral).

As used herein, a hemi-labile ligand refers to a ligand that has at least two coordinating atoms, one that is weakly associated to the metal center and one that is more strongly associated to the metal center. In accordance with the present invention, the coordinating atoms are not identical and, the weaker coordinating atom can be displaced by a second ligand, such as an analyte or an allosteric effector, whereas the stronger coordinating atom remains coordinated to the metal center of the coordination complex. The coordinating atom can be, but not limited to, phosphorus, nitrogen, sulfur, and oxygen.

One non-limiting example of a hemi-labile ligand is a ligand that contains both a sulfur atom (the weak coordinating atom) and a phosphorus atom (the strong coordinating atom). Other non-limiting examples include ligands having nitrogen and oxygen coordinating atoms. One achiral ligand and an example of coordination complexes contemplated in the present invention are:

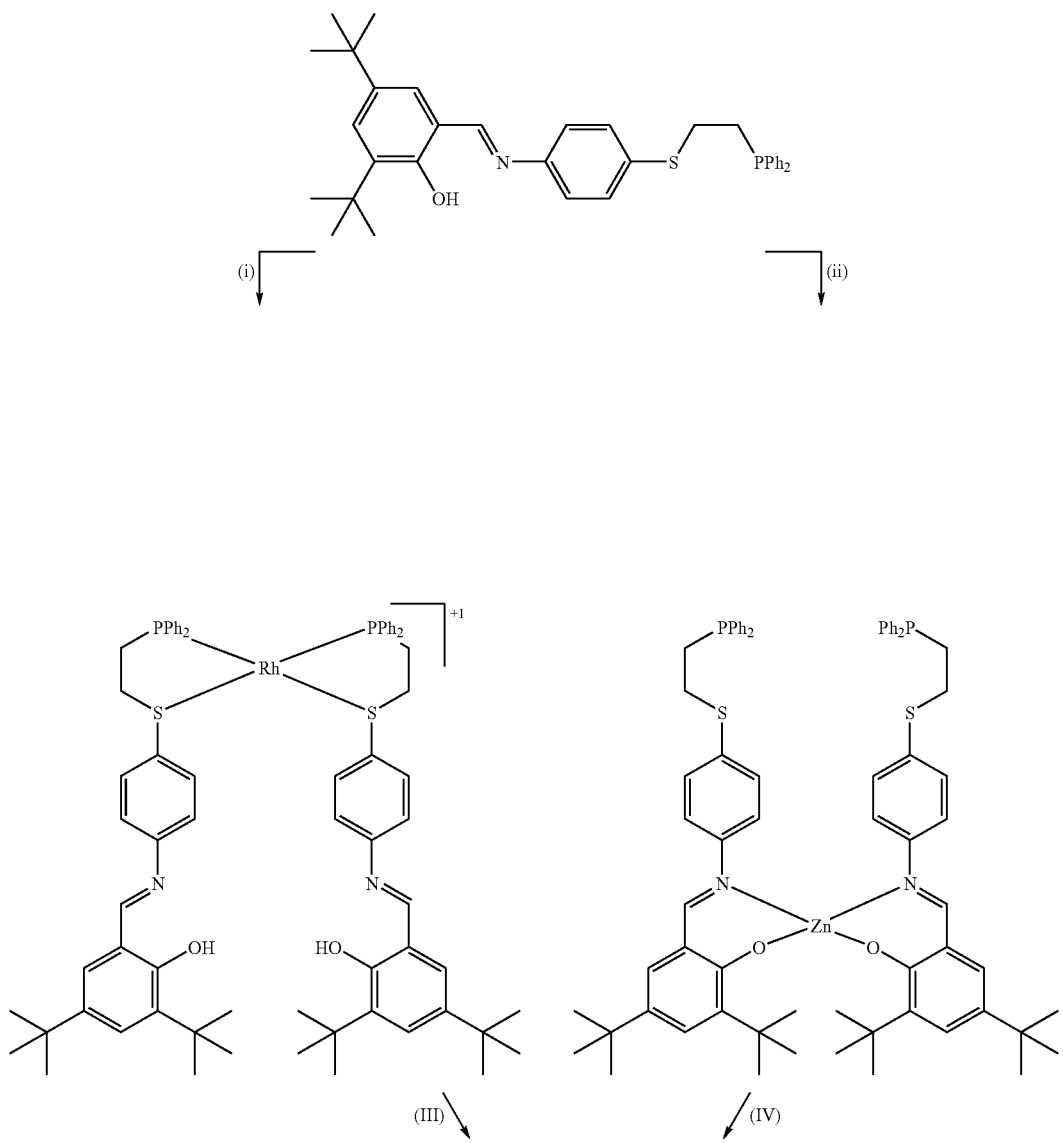

-continued

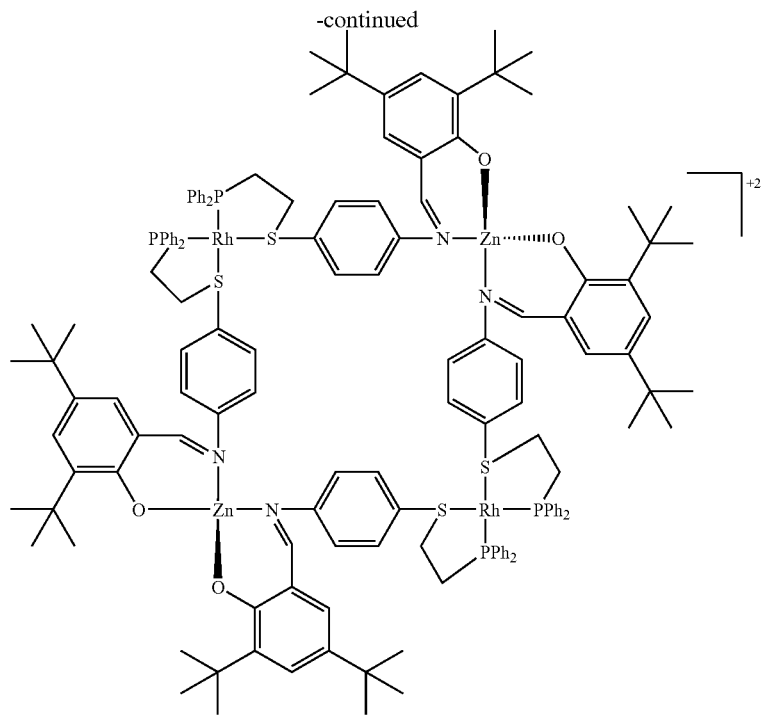

The hemi-labile ligand also can optionally include a chiral backbone that allows for selective binding of one enantiomer of an analyte or allosteric effector over another. Nonlimiting examples of chiral backbones include 1,1'-binaphthol (BINOL) (Mikami et al. *J. Am. Chem. Soc.* 111:1940 (1989)), 2,2'-bis(diphenylphosphino)-1,1'-binaphthyl (BINAP) (Miyashita et al. *J. Am. Chem. Soc.* 102:7932 (1980)); salen-based complexes (i.e., coordinatino complexes containing the N,N-bis(3,5-di-t-butylsalicylidene)-1,2-cyclohexane-diamino ligand; see, e.g., Li et al. *J. Am. Chem. Soc* 115:5326 (1993), variations of the salen ligand (e.g., free nitrogen version of salen or a salen ligand motif), and Evans et al. *Tetrahedron Lett.* 34:7027 (1993)), bisoxazoline-containing compounds (Evans et al. *J. Am. Chem. Soc.* 115:6460 (1993)), taddol, and tartrate esters. Nonlimiting examples of salen-based ligand and the corresponding coordination complexes, both macrocyclic and tweezer, are shown below.

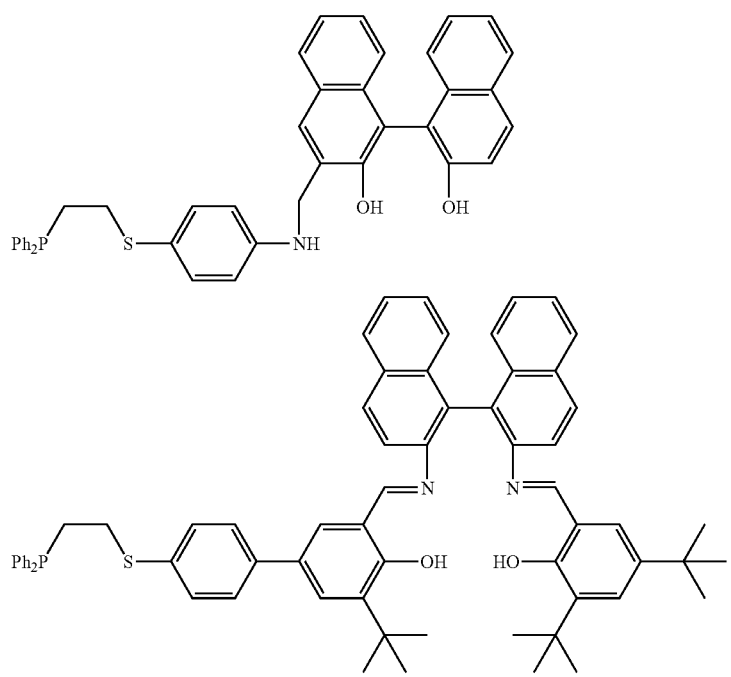

-continued
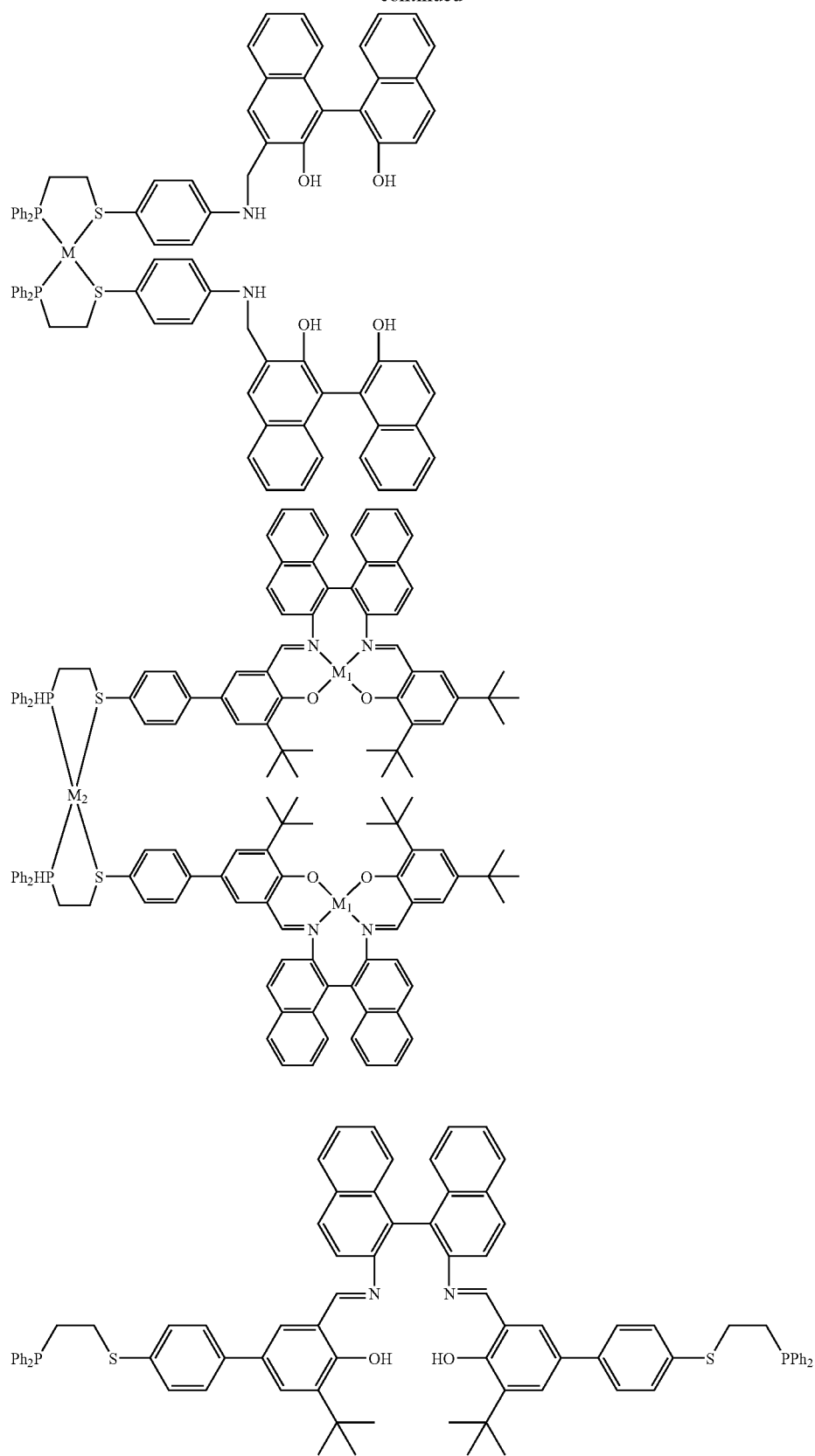

-continued

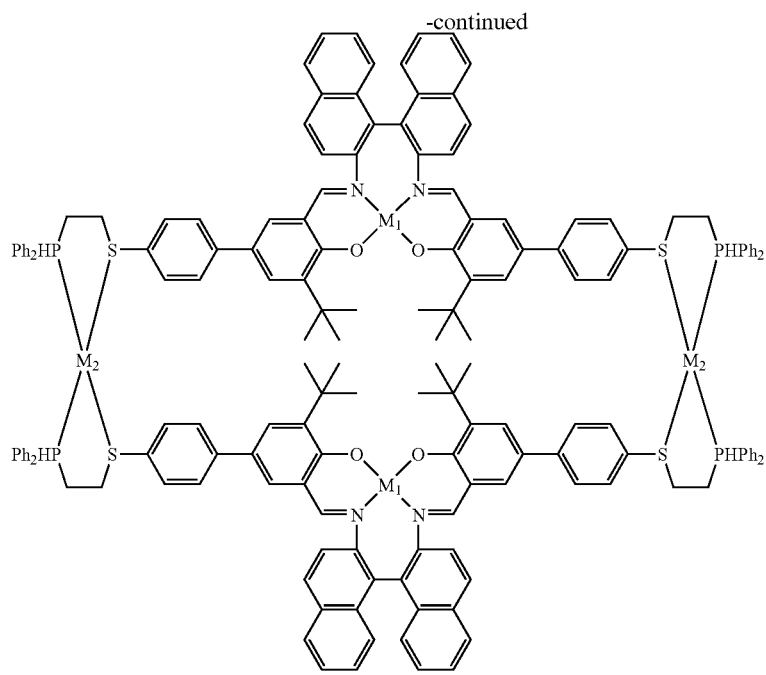

As used herein, an allosteric effector is any molecule that can coordinate to a metal center of a coordination complex and effects a structural conformation change in the coordination complex (i.e., from conformation A to conformation B). An analyte is a molecule of interest. In some embodiments, the allosteric effector is the analyte. In other embodiments, the allosteric effector is different from the analyte, but effects detection of the analyte of interest. In some embodiments, the analyte is a substrate of a catalytic reaction. In other embodiments, the analyte is a molecule that coordinates to specific structural conformations of a coordination complex, but not other structural conformations. In still other embodiments, the analyte is both the allosteric effector and the substrate of a catalytic reaction.

In some embodiments, the allosteric effector is an allosteric protagonist. An allosteric protagonist is a ligand that effects a structural conformation change of the coordination complex and activates the catalytic activity of the coordination complex or allows for coordination of the analyte of interest to the metal center. In other embodiments, the allosteric effector is an allosteric antagonist. An allosteric antagonist is a ligand that effects a structural conformation change to the coordination complex and deactivates the catalytic activity of the coordination complex or prevents coordination of the analyte of interest.

Non-limiting examples of allosteric effectors include CO, $SO_2$, $CH_3CN$, $H_2N-R-NH_2$, $R^1HN-R-NHR^1$, NC—R—CN, R—CN, NC—R—NC, heteroaryl, and CN—, wherein R is selected from the group consisting of optionally substituted linear or branched $C_{1-8}$alkyl, linear or branched $C_{2-8}$alkenyl, linear or branched $C_{2-8}$alkynyl, aryl, $C_{3-8}$cycloalkyl, and $C_{3-8}$cycloalkenyl; and $R^1$ is the same or different and is selected from the group consisting of hydrogen and linear or branched $C_{1-8}$alkyl. Specific nonliming examples of allosteric effectors are illustrated below.

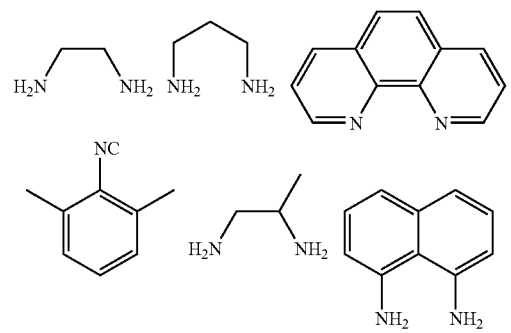

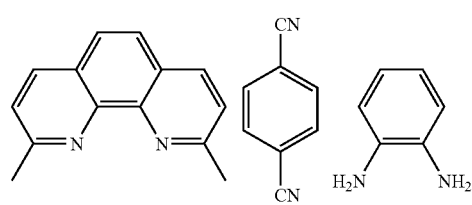

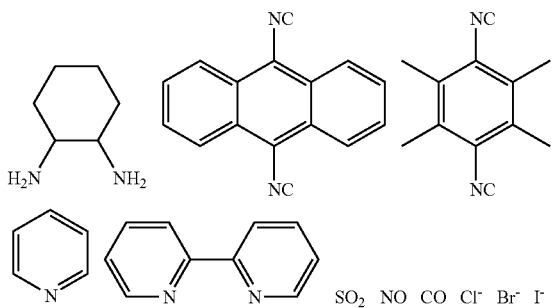

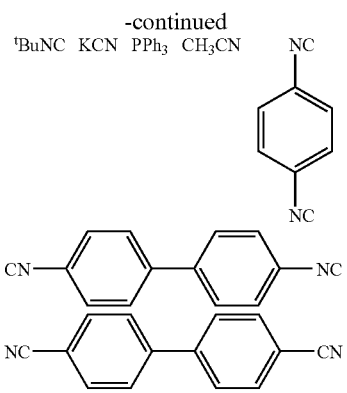

As used herein, $C_{1-8}$alkyl refers to a linear or branched saturated hydrocarbon group containing 1 to 8 carbon atoms, for example methyl, ethyl, n-propyl, isopropyl, n-butyl, isobutyl, t-butyl, octyl, and the like. $C_{3-8}$cycloalkyl refers to a ring having 3 to 8 carbon atoms, for example cyclopentyl, cyclohexyl, and the like.

As used herein, $C_{2-8}$alkenyl refers to a linear or branched hydrocarbon group having 2 to 8 carbon atoms and having at least one carbon-carbon double bond, for example ethenyl, n-propenyl, isopropenyl, n-butenyl, isobutenyl, octenyl, and the like.

As used herein, $C_{2-8}$alkynyl refers to a linear or branched hydrocarbon group having 2 to 8 carbon atoms and having at least one carbon-carbon triple bond, for example ethynyl, propynyl, 1-butynyl, 2-butynyl, octynyl, and the like.

$C_{3-8}$cycloalkenyl is defined identically to $C_{3-8}$cycloalkyl, except the ring contains at least one carbon-carbon double bond.

The term halo and halide are used in the conventional sense to refer to a chloro, bromo, fluoro, or iodo substituent or corresponding ion.

As used herein, aryl is an aromatic moiety generally containing 6 to 30 carbon atoms. An aryl group can contain a single aromatic ring or multiple aromatic rings that are fused together, directly linked, or indirectly linked (such that the different aromatic rings are bound to a common group such as a methylene or ethylene moiety). Preferred aryl groups contain 6 to 20 carbon atoms, and particularly preferred aryl groups contain 6 to 12 carbon atoms. Exemplary aryl groups contain one aromatic ring or two fused or linked aromatic rings, e.g., phenyl, naphthyl, biphenyl, diphenyl ether, diphenylamine, benzophenone, and the like. Aryl groups can optionally be substituted with one or more substituent groups. Nonlimiting examples of substituent groups include halo, nitro, cyano, linear or branched $C_{1-8}$alkyl, linear or branched $C_{2-8}$alkenyl, aryl, $C_{3-8}$cycloalkyl, $C_{3-8}$cycloalkenyl, amino, amido, carboxylate, and hydroxy.

As used herein, heteroaryl is an aromatic moiety as defined above for aryl, and that further contains at least one ring heteroatom selected from the group consisting of oxygen, nitrogen, and sulfur. Non-limiting examples of heteroaryl groups include pyrrolyl, pyrrolidinyl, pyridinyl, quinolinyl, indolyl, pyrimidinyl, imidazolyl, 1,2,4-triazolyl, tetrazolyl, 2,2'-bipyridinyl, and pyridine[3,2,h]quinolinyl.

One embodiment of the present invention is the use of a coordination complex to identify an analyte of interest, and particularly, one enantiomer of a chiral analyte, as illustrated below. For example, the binaphthyl metallocyclophanes, termed (S)-3 and (S)-4, have been designed to allosterically recognize chiral α-hydroxy carboxylic acids. (S)-4 has two different binding sites, but (S)-3, because of its condensed nature, only has one. In the case of (S)-4, one binding site is a Cu(P,S)2 site that allows for allosteric regulation by reaction with 2,2'-bipyridyl (2,2'-bipy). The other binding site is a hydrogen bonding site for chiral guest molecules, such as mandelic acid derivatives. Therefore, as (S)-3 is converted to (S)-4 through a reaction between 2,2'-bipy and the allosteric Cu(I) regulatory site, a chiral recognition pocket is generated. This structure was designed based upon its resemblance to a bisbinaphthyl macrocycle, an organic structure known to selectively recognize enantiomers of mandelic acid (Lin et al, *Org. Lett.*, 4:3297 (2002)).

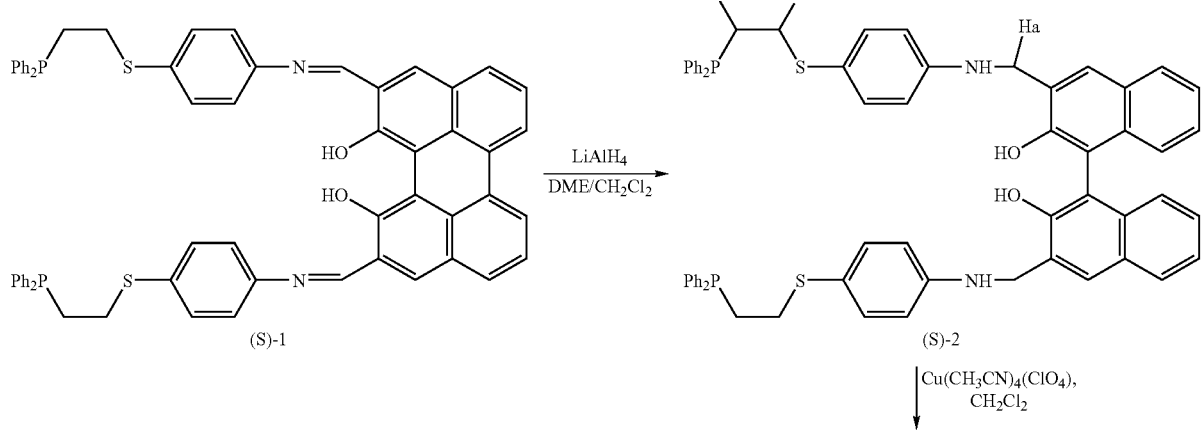

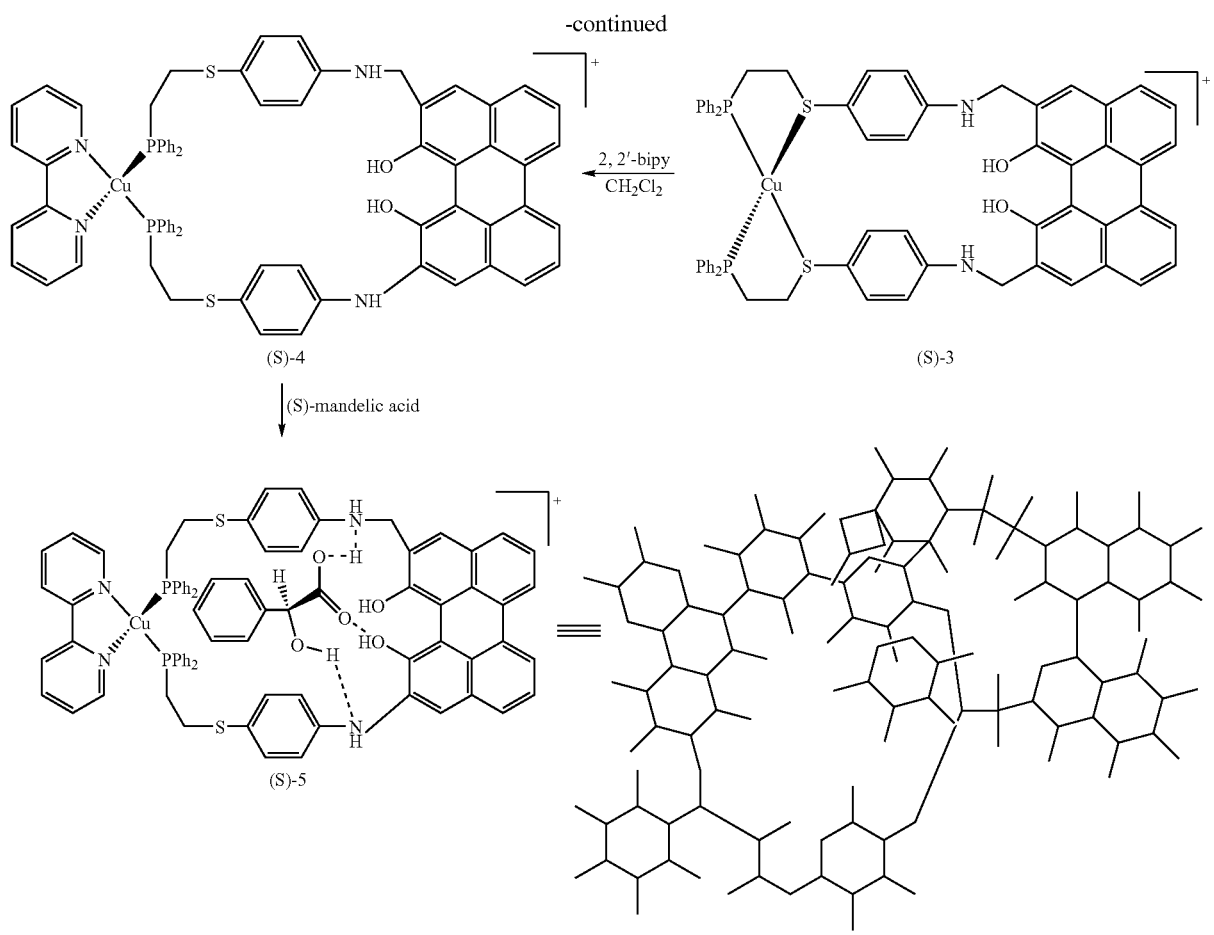

Another embodiment of the present invention is the use of a present coordination complex having a hemi-labile ligand to effect a change in the catalytic ability of the coordination complex. The invention includes the design, synthesis and application of an allosterically activated catalyst. The artificial allosteric catalyst can be switched from a deactivated to an activated state by the introduction of allosteric protagonists. These protagonists take the form of molecules, ions, or any input signal, such as electromagnetic radiation, capable of effecting a change in conformation of the catalyst, which, in turn, results in a change in catalyst activity and/or selectivity. The species that influences the catalyst is a protagonist or antagonist for positive or negative effects, respectively, on catalyst selectivity or rate of reaction.

The activated catalyst of the coordination complex as described above allows for the amplification of an analyte signal via coupling with a catalytic cycle detection step. In some embodiments, the catalyst effects the production of a product that can be detected. In other embodiments, the analyte is both the allosteric effector and the substrate for the catalytic reaction. Whereas the amount of the catalyst remains constant, the amount of product increases and detection of the analyte is facilitated. The analyte can bind to only one coordination complex molecule, but the product that is detected is produced in larger quantities, allowing for smaller amounts of analyte to be detected due to this amplification of a detectable signal. This concept is schematically represented in FIG. 1, wherein the analyte of interest plays the role of the allosteric effector and a product of the catalytic reaction is detected. In this example, the production of acetic acid is detected by the change in fluorescence of a sensor molecule.

Detection of the analyte can occur through various means. When binding of the analyte activates the catalytic activity of the coordination complex, detection of the analyte can be measured indirectly by detecting the presence of a product of the catalytic reaction (or consumption of a starting material). Detection can occur by measuring changes in fluorescence, pH, temperature, or color, for example, or by using chromatography techniques such as high pressure liquid chromatography (HPLC), gas chromatography (GC), and the like. Measurement of the production of a product or consumption of a starting material is dependent upon the particular catalytic reaction taking place, and the best means for detecting such will be apparent to persons of skill in the art.

More particularly, one means of indirect detection of an analyte of interest via a product of a catalytic reaction is illustrated in FIG. 1. A coordination complex having two domains containing rhodium(I) (Rh(I)) metal centers and a catalytic domain containing two zinc(II) (Zn(II)) metal centers is shown. The macrocyclic cavity of the coordination complex can be opened to form an open coordination complex by the introduction of carbon monoxide gas (CO, 1 atmosphere (atm)) in the presence of chloride ions, Cl⁻, (benzyltriethylammonium chloride) in methylene chloride. Both CO and Cl⁻ are required to break the thioether/Rh(I) bonds, leaving the phosphine/Rh(I) bonds intact. The result of the selective breaking of these bonds is a concomitant, significant change in the molecular shape. This change in molecular shape (FIG. 1) corresponds to a change in the catalytic activity of the catalyst (i.e., $k_1 \lll k_2$, wherein $k_1$ is the rate of reaction of the closed coordination complex and $k_2$ is the rate of reaction of the opened coordination complex). The acyl transfer reaction between acetic anhydride and pyridyl carbinol is much faster in the presence of the open, activated structural conformation. It is hypothesized, but not relied upon herein, that this reaction rate is faster because of the bimetallic catalytic nature of the open structural conformation. A pH dependent sensor molecule (e.g., 9-anthryl-N,N-diethylmethanamine) allows for easy detection of the production of acetic acid.

Figure 2:
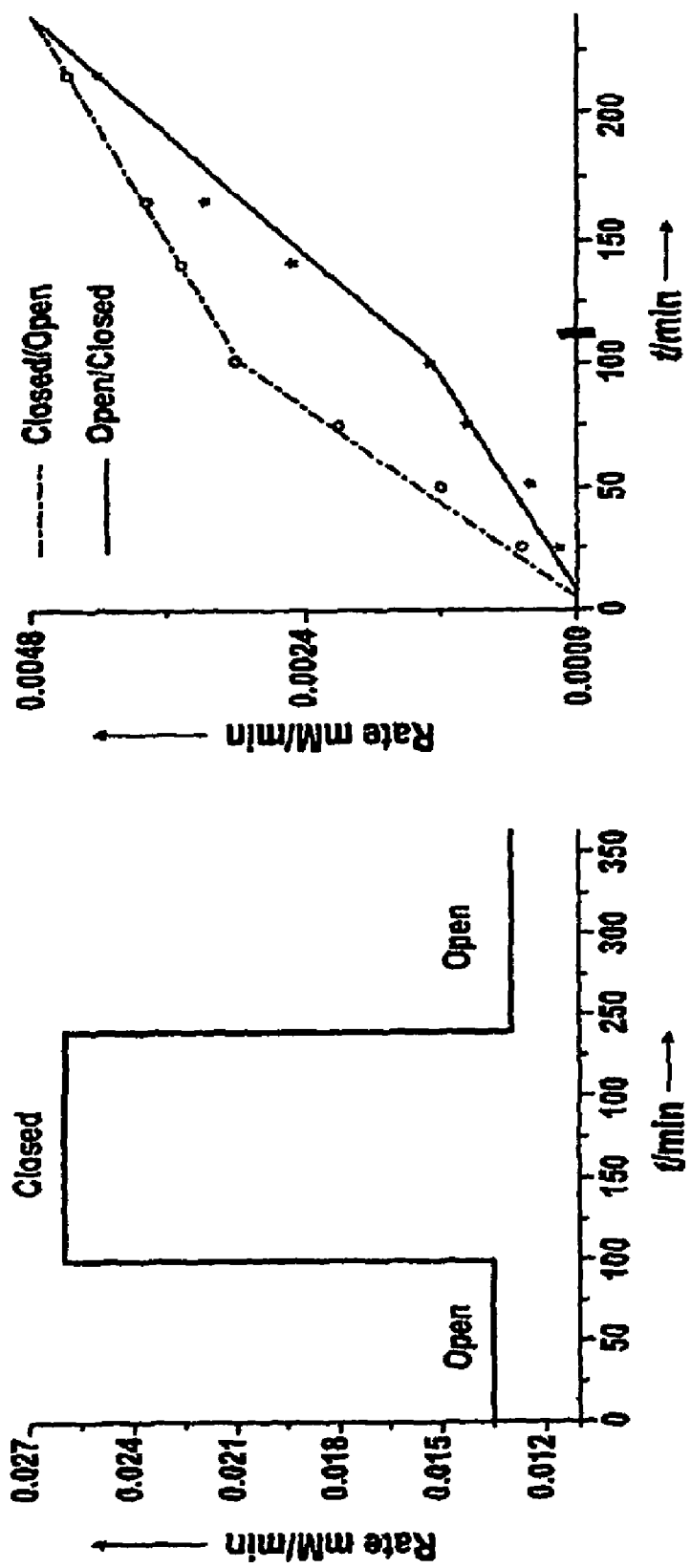
FIG. 2 illustrates the activation and deactivation of a coordination complex as a catalyst in the presence and absence of an allosteric effector.

In another embodiment, a fixed U-shaped (i.e., tweezer) coordination complex in combination with an allosteric effector can be activated or deactivated as a catalyst, allowing for the detection of an analyte of interest. This activation/deactivation of the catalytic ability of a coordination complex shown below (deactivated, below structure 3; activated, top structure 2) is illustrated in FIG. 2 for the reaction of the asymmetric ring opening of cyclohexene oxide by azidotrimethylsilane (TMSN$_3$). In FIG. 2, left graph, the coordination complex is an active catalyst when the hemi-labile ligand is fully coordinated to the metal center ("closed," complex 2, below), and deactivated as a catalyst by CO saturation ("open," complex 3, below). The coordination of CO to the metal center causes the coordination complex to change structural conformations from the closed, U-shaped, active catalyst structural conformation to the open, inactive catalyst structural conformation. The formation of a product of the catalytic reaction is monitored, as illustrated by the graph on the right. The activation and deactivation of the coordination complex is translated to the rate of production of the product and to the enantiomeric excess (% ee) observed.

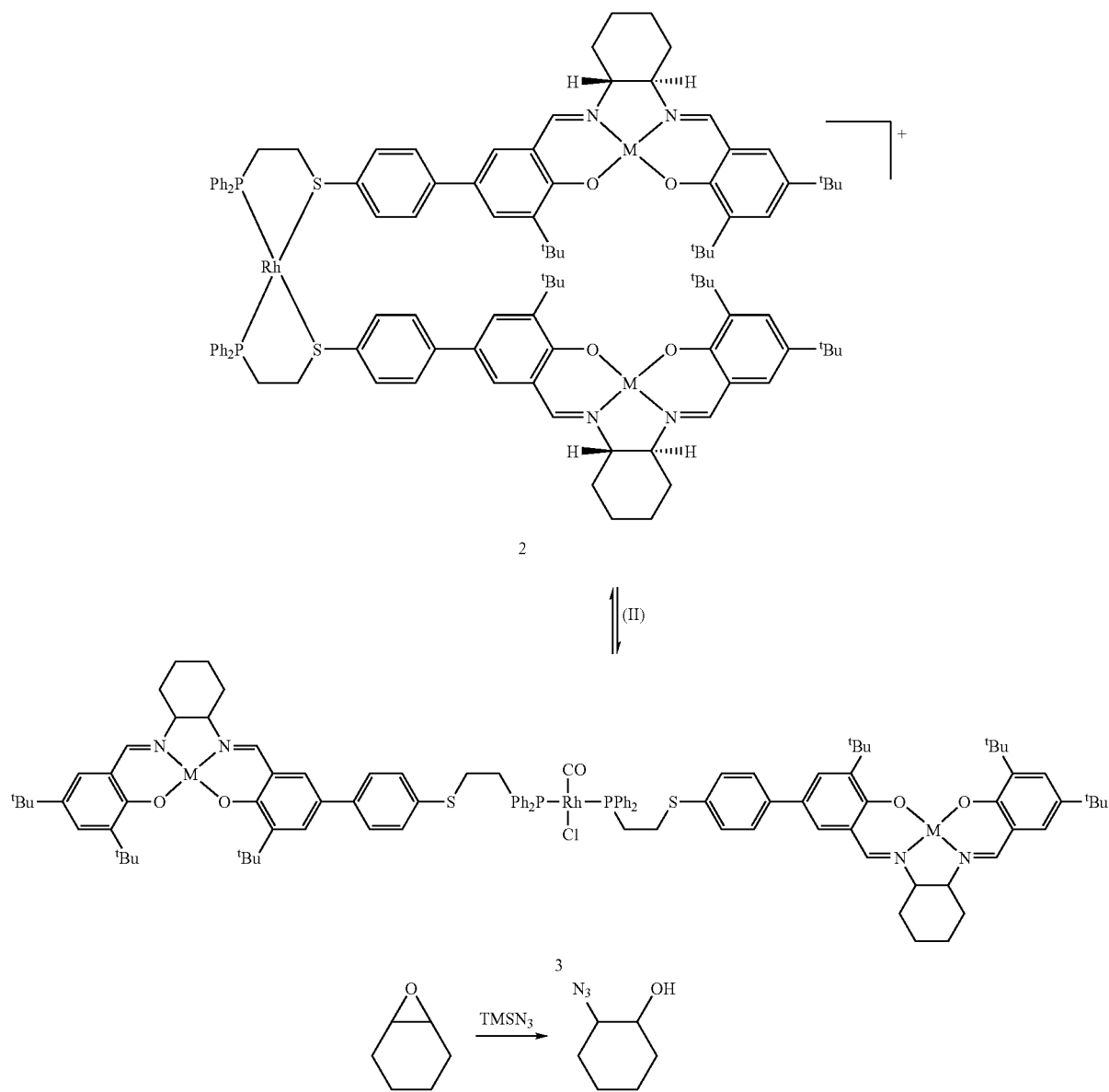

In cases where binding of the analyte to the coordination complex does not trigger a catalytic reaction, analyte detection can be achieved by monitoring spectroscopic changes in the coordination complex. For example, changes in fluorescence can be measured to monitor binding of the analyte to the coordination complex. Chromatographic methods also can be employed to measure binding of the analyte, for example size-exclusion chromatography, and the like. Other means of analyzing a sample can be employed such as mass spectrometry, raman spectroscopy nuclear magnetic resonance, and the like.

In some embodiments, sensor molecules can be added to the sample as a means of detecting the analyte. One non-limiting example of such a sensor molecule is a fluorescent probe that changes fluorescence depending upon the pH of the sample. See FIG. 1, wherein the generation of acetic acid protonates the sensor molecule, which is highly fluorescent Other types of sensor molecules also can be used depending upon the analyte of interest.

When the analyte is chiral, another embodiment of the present invention is a selective binding of the analyte enantiomer of interest to the coordination complex compared to the other enantiomer. In such cases, the structural conformation that allows for binding of a chiral analyte has a coordination site that preferentially complexes with the enantiomer of interest. The analyte enantiomer of interest binds to the coordination complex more preferentially than the other enantiomer, which also permits the separation of enantiomers.

Examples

Synthetic Methods

All reactions were carried out under an inert atmosphere of nitrogen using standard Schlenk techniques or an inert atmosphere glovebox unless otherwise noted. Methylene chloride ($CH_2Cl_2$) and pentane were dried and distilled over calcium hydride. All solvents were degassed via nitrogen gas ($N_2$) bubbling prior to use. 2,2'-Dihydroxy-[1,1']-binaphthalenyl-3,3'-dicarbaldehyde was prepared via a literature procedure (Zhang et al., *J. Org. Chem.*, 66:481 (2001)). Deuterated solvents were purchased from Cambridge Isotope Laboratories Inc. (Andover, Mass.) and used as received. All other chemicals were used as received from Aldrich Chemical Company (Milwaukee, Wis.). Proton nuclear magnetic resonance ($^1H$ NMR) and proton-decoupled carbon nuclear magnetic resonance ($^{13}C\{^1H\}$ NMR) spectra were recorded on a Varian Mercury 300 MHz FT-NMR spectrometer and referenced relative to TMS resonances in deuterated chloroform ($CDCl_3$) and to residual proton resonances in deuterated methylene chloride ($CD_2Cl_2$). Proton decoupled phosphorus nuclear magnetic resonance ($^{31}P\{^1H\}$ NMR) spectra were recorded on a Varian Mercury 300 MHz FT-NMR spectrometer at 121.4 MHz and referenced relative to an external 85% phosphoric acid standard. All chemical shifts are reported in ppm. UV-V is spectra were recorded on a Varian Cary 50 Bio spectrophotometer in HPLC grade acetonitrile. Circular dichroism (CD) spectra were recorded on a Jasco J-715 spectrometer. Electrospray mass spectra (ESI-MS) were recorded on a Micromas Quatro II triple quadrapole mass spectrometer. Electron ionization mass spectra (EI-MS) were recorded on a Sisions VG 70-250 SE mass spectrometer. Elemental analyses were performed by Quantitative Technologies Inc., Whitehouse, N.J.

Preparation of Macrocyclic Coordination Complexes

The synthesis of the hemi-labile ligand and corresponding coordination complex outlined below can be used to synthesize other hemi-labile ligands and coordination complexes by variation of the starting materials, such as using a different dialdehyde. The appropriate choice of starting materials to synthesize a hemi-labile ligand will be readily apparent to one of skill in the art in view of the examples set forth below.

Enantiomerically pure (S)-BINOL-3,3'-dicarbaldehyde and 4-(2-diphenylphosphanylethylthio)phenylamine were coupled via imine condensation to give compound (S)-1 which was reduced with lithium aluminum hydride to give a new amine compound (S)-2 in moderate yield. One equivalent of ligand (S)-2 was reacted with one equivalent of Cu(I) perchlorate tetraacetonitrile in $CH_2Cl_2$ to form the condensed intermediate (S)-3. Compound (S)-3 reacts with 2,2'-bipy (one equivalent) to cleanly yield (S)-4 in $CH_2Cl_2$. The synthetic procedure for (S)-1, (S)-2, (S)-3, and (S)-4 are as follows.

3,3'-Bis-{[4-(2-diphenylphosphanyl-ethylthio)-phenylimino]-methyl}-[1,1']binaphthylenyl-2,2'-diol, (S)-1, was prepared according to the following procedure. 2,2'-Dihydroxy-[1,1']binaphthylenyl-3,3'-dicarbaldehyde (700 mg, 2.04 mmol), 4-(2-diphenylphosphanyl-ethylthio)phenylamine (1-38 g, 4.10 mmol), $CH_2Cl_2$ (30 mL), and methanol ($CH_3OH$) (50 mL) were added to a Schlenk flask. The resulting solution was refluxed for 24 hours (h). The solution was dried in vacuo, and the resulting orange solid was purified by column chromatography (eluent $CH_2Cl_2$). The yield was 1.94 g (95%). $^1H$ NMR ($CD_2Cl_2$). δ 13.11 (s, 2H, OH), 8.85 (s, 2H, N=CH), 8.09 (s, 2H, aromatic), 7.87 (m, 2H, aromatic), 7.35-7.11 (m, 34H, aromatic), 2.89 (m, 4H, $H_2C$—S), 2.30 (m, 4H, $H_2C$—P). $^{13}C\{^1H\}$ NMR ($CD_2Cl_2$): δ 162.57 (s), 154.74 (s), 146.12 (s), 138.01 (d, $J_{P-C}$=13.5 Hz), 135.75 (d, $J_{P-C}$=15.8 Hz), 132.96 (br m), 130.02 (br m), 128.82 (br m), 127.93 (s), 124.77 (br m), 123.80 (br m), 121.99 (br m), 121.54 (s), 117.01 (s), 30.31 (d, $J_{P-C}$=24.0 Hz), 28.28 (d, $J_{C-P}$=16.5 Hz). $^{31}P\{^1H\}$ NMR ($CD_2Cl_2$): δ −16.3 (s). EI-MS (m/z) Calcd: 980.28. Found: 981.4. Anal. Calcd for $C_{62}H_{50}N_2O_2P_2S_2H_2O$: C, 74.53; H, 5.25; N, 2.80. Found: C, 74.43; H, 5.00; N, 2.78.

3,3'-Bis-{[4-(2-diphenylphosphanyl-ethylsulfanyl)-phenylamino]-methyl}-[1,1']binaphthylenyl-2,2'-diol, (S)-2, was prepared according to the following procedure. (S)-1 (3.477 g, 3.48 mmol) in $CH_2Cl_2$/dimethoxyethane (DME) (30 mL/30 mL) was reacted with lithium aluminum hydride (3.0 equivalents) at 0° C. The reaction mixture was stirred overnight at room temperature and quenched with water (20 mL). Volatiles were evaporated under reduced pressure and more water (100 mL) was added. The mixture was extracted with $CH_2Cl_2$ (3 times, 100 mL). The combined organic layers were washed with brine and water, concentrated under reduced pressure and then dried with sodium sulfate. Filtration and purification by column chromatography gave monohydrated amine ligand as a yellowish solid (eluent, $CH_2Cl_2$). Yield 2.19 g (63%). $^1H$ NMR ($CD_2Cl_2$): δ 7.86 (s, 2H, aromatic), 7.76 (d, 2H, aromatic), 7.27-7.11 (m, 28H, aromatic), 6.98 (d, 2H, aromatic), 6.66 (d, 4H, aromatic), 4.54 (s, 4H, $H_2C$—NH); 2.76 (m, 4H, $CH_2$—S), 2.20 (m, 4H, $H_2C$—P). $^{13}C\{^1H\}$ NMR ($CD_2Cl_2$): δ 152.03 (s), 147.37 (s), 138.23 (d, $J_{P-C}$=14.3 Hz), 133.91 (br m), 133.34 (s), 132.89 (br m), 129.25 (br m), 128.80 (br m), 126.93 (s), 124.40 (br m), 123.51 (s), 115.04 (br m), 113.39 (s), 46.20 (s), 32.81 (s), 28.41 (s). $^{31}P\{^1H\}$ NMR ($CD_2Cl_2$): δ −16.9 (s). EI-MS (m/z): Calcd: 985.2. Found: 985.2. Anal. Calcd for $C_{62}H_{54}N_2O_2P_2S_2H_2O$: C, 74.23; H, 5.63; N, 2.79. Found: C, 74.22; H, 5.44; N, 2.68.

[μ-(3,3'-Bis-{[4-(2-diphenylphosphanyl-ethyldulfanyl)-phenylamino]-methyl}-[1,1']binaphthalenyl-2,2'-diol)Cu][ClO₄], (S)-3, was prepared according to the following procedure. In a Schlenk flask, the ligand (S)-2 (295 mg, 0.299 mmol) was dissolved in $CH_2Cl_2$ (10 mL). A solution of copper (1) perchlorate tetraacetonitrile $[Cu(MeCN)_4](ClO_4)$ (98 mg, 0.300 mmol) in $CH_2Cl_2$ (10 mL) was added via cannula to the stirring ligand solution to give a colorless solution. After stirring for 12 h, solvent was removed under reduced pressure, and the resulting white solid was dried at 150° C. under vacuum to give a yellowish sticky solid. Recrystallization from $CH_2Cl_2$/diethyl ether ($Et_2O$) afforded an analytically pure compound (as determined by NMR spectroscopy) in quantitative yield (322 mg, 94%). $^1H$ NMR ($CD_2Cl_2$): δ 7.75 (s, 2H, aromatic), 7.68 (d, 2H, aromatic), 7.25-6.92 (m, 28H, aromatic), 6.45 (s, 4H, aromatic), 4.41 (br, 4H, $H_2C$—NH), 2.89 (br, 4H, $H_2C$—S), 2.42 (br, 4H, $H_2C$—P). $^{13}C\{^1H\}$ NMR ($CD_2Cl_2$): δ 151.71 (s), 149.50 (s), 134.49 (br, m), 133.07 (s), 132.50 (br m), 130.88 (br m), 129.29 (br m), 127.05 (s), 126.76 (m), 124.19 (br m), 116.32 (m), 114.47 (br m), 112.85 (s), 100.09 (s), 44.99 (br m), 38.15 (br m), 28.56 (br m). $^{31}P\{^1H\}$ NMR ($CD_2Cl_2$): δ –0.2 (s). ESI-MS (m/z) Calcd: 1047.2. Found: 1047.2. Anal. Calcd for $C_{62}H_{54}N_2O_6P_2S_2Cl_1Cu\cdot H_2O$: C, 63.85; H, 4.84; N, 2.40. Found: C, 64.07; H, 4.77; N, 2.40.

[μ-(3,3'-Bis-{[4(2-diphenylphosphanul-ethylsulfanyl)-phenylamino]-methyl}-[1,1']binaphthylenyl-2,2'-diol)Cu-$η^2$-(2,2-bipyridine)][$ClO_4$], (S)-4, was prepared according to the following procedure. In a Schlenk flask, copper complex (S)-3 (103 mg, 0.0897 mmol) and 2,2'-bipyridine (14 mg, 1 equivalent) were dissolved in $CH_2Cl_2$ (5.0 mL) to give a yellow solution. After stirring for 1 h, the solvent was removed to yield analytically pure yellow solid in quantitative yield (114 mg, 97%) $^1H$ NMR ($CD_2Cl_2$): δ 7.86 (m, br, 8H, aromatic), 7.57 (s, br, 2H, aromatic), 7.31-7.11 (m, 22H, aromatic), 6.99 (s, br, 2H, aromatic), 6.90 (s, br, 4H, aromatic), 6.52-6.49 (m, 4H, aromatic), 4.74 (d, 2H, $^3J_{H-H}$=13.8 Hz, $H_2C$—NH, 4.36 (d, 2H, $^3J_{H-H}$=14.4 Hz, $H_2C$—NH), 1.86 (br, 4H, $H_2C$—S), 1.82 (br, 8H, $H_2C$—P). $^{13}C\{^1H\}$ NMR ($CD_2Cl_2$): δ 153.19 (s0, 148.75 (s), 139.95 (br m), 135.76 (br m), 134.41 (s), 132.87 (br m), 132.34 (br m), 129.68 (br m), 127.84 (s), 126.72 (br m), 124.12 (br m), 121.31 (s), 115.31 (br m); 46.74 (br m), 32.41 (br m), 28.19 (br m). $^{31}P\{^1H\}$NMR ($CD_2Cl_2$): δ –6.4 (s). ESI-MS (m/z) Calcd: 1203.3. Found: 1203.4. Anal. Calcd for $C_{72}H_{62}N_4O_6P_2S_2Cl_1Cu\ H_2O$: C, 65.40, H, 4.88; N, 4.24. Found: C, 65.67; H, 4.87; N, 4.30.

The formation of (S)-4 was confirmed by an upfield shift of the $^1H$ NMR resonances for the methylene groups of the chelating arms of the tetradentate ligand —$SCH_2CH_2PPh_2$. These resonances shift from δ 3.00 and 2.53 to δ 1.86 and 1.83, respectively. The BINOL-$CH_2NH_2$— resonances exhibit peak-splitting (Kovbasyuk et al., *Chem. Rev.*, 104: 3161 (2004); Nabeshima et al., *Inorg. Chem.*, 32:1407 (1993)) that is highly diagnostic of a chiral macrocycle (from a singlet at δ 4.46 to two doublets at δ 4.80 and 4.43). The $^{31}P\{^1H\}$ NMR spectroscopy of (S)-4 also is consistent with that of a symmetric $CuP_2$(phenanthroline) complex with a singlet at –6.4 ppm. All other data including ESI mass spectroscopy and elemental analyses are consistent for the proposed structures.

Figure 3:
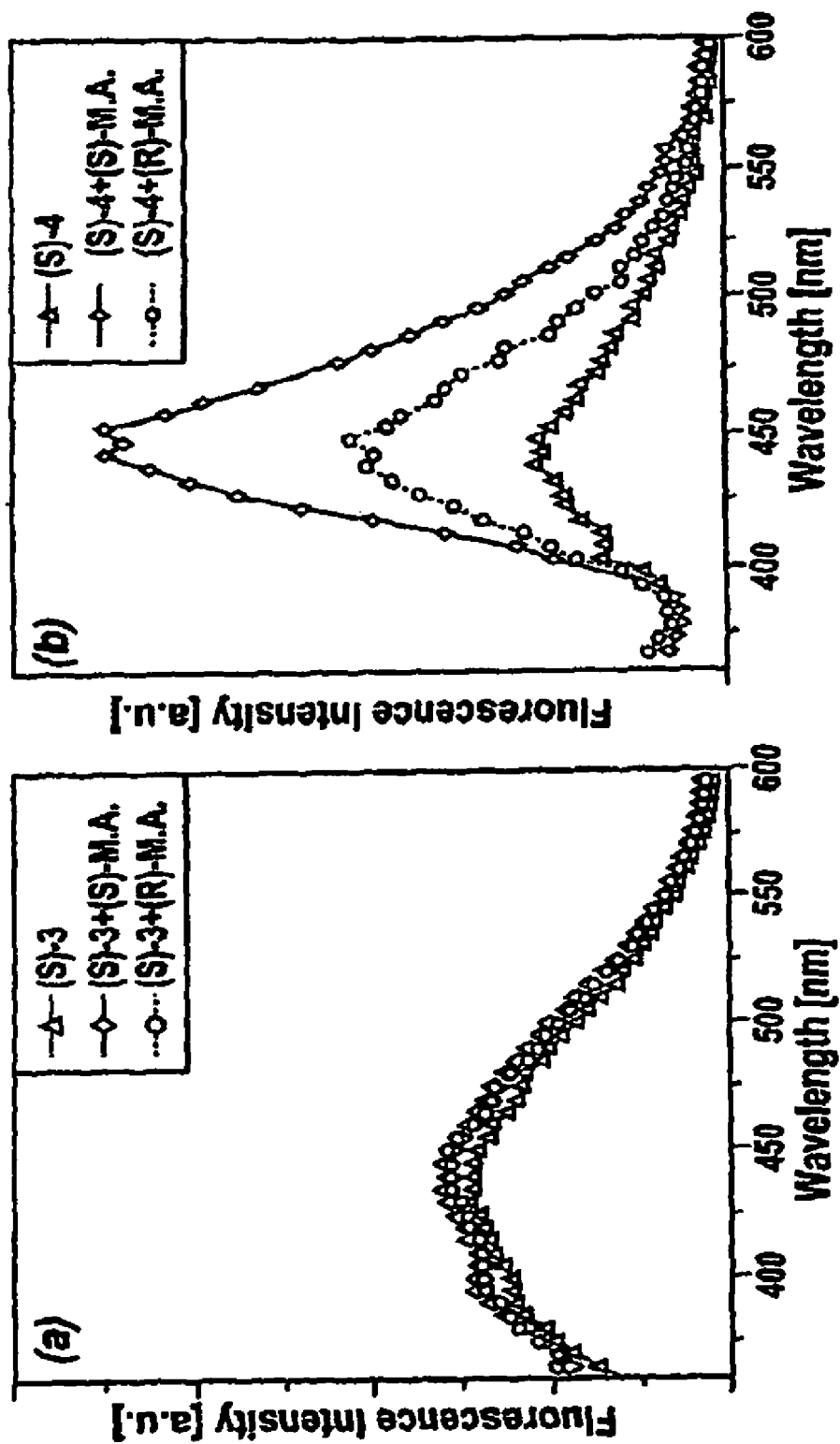
FIG. 3 shows the fluorescence spectra of a coordination complex in the presence of an analyte before (FIG. 3(a)) and after (FIG. 3(b)) coordination of an allosteric effector and its enantiomer.

The CD spectrum of (S)-2 exhibits a characteristic positive couplet, which is similar to that of (S)-BINOL, due to the exciton coupling between the long axis polarized $^1B_h$ transition, with a positive maximum at 237 nm, and a negative minimum at 226 nm. A further negative bond at 205 nm was observed and corresponds to a higher energy $^1B_h$ transition (Peacitelli et al, *Organometallics*, 23:4223 (2004); Rosini et al., *Eur. J. Org. Chem.*, 61 (2000); Hug et al., *J. Am. Chem. Soc.*, 96:3407 (1974). (S)-3 and (S)-4 displayed additional positive maxima at 270 nm that can be attributed to a chiral arrangement of the $PPh_2$ group on the Cu(I) center. The CD spectra of (S)-3 and (S)-4 are very similar, suggesting that there is very little change in the chirality and dihedral angle of the BINOL center. (FIG. 3).

Chiral Recognition Using Macrocyclic Coordination Complexes

To study the allosteric effect of the macrocyclic coordination complexes, closed complex (S)-3 and open complex (S)-4 were independently treated with both enantiomers of mandelic acid and monitored by fluorometry (Pu et al, *Chem. Rev.*, 104:1687 (2004); Xu et al., *J. Am. Chem. Soc.*, 124: 14239 (2002); Lin et al., *J. Am. Chem. Soc.*, 124:2008 (2002); Lin et al., *Org. Lett.*, 4:3297 (2002)). First, (S)-3 (0.10 mM) was treated with a 50-fold excess of (S)- or (R)-mandelic acid (5.0 mM). In both cases, no significant changes in fluorescence were observed (FIG. 3(*a*)). This is because the binding pocket is closed and the multiple hydrogen bonding sites required to complex mandelic acid are not accessible.

In contrast, open complex (S)-4 can accommodate mandelic acid, and the fluorescence intensity of (S)-4 increases in the presence of (S)- or (R)-mandelic acid. This increase in fluorescence is due to the suppressed photo-induced electron transfer fluorescence quenching as the amine nitrogen of (S)-4 is protonated by the acid (FIG. 6B) (peacock et al, *J. Am; Chem. Soc.*, 102:2043; (1980); Naruta et al., *J. Am. Chem. Soc.*, 113:6865 (1991); Kubo et al, *Nature*, 382:521 (1996); Hu et al., *J. Am. Chem. Soc.*, 125:11490 (2003); Lee et al, *J. Am. Chem. Soc.*, 124:12948 (2002); Lee et al., *J. Am. Chem. Soc.*, 124:4554 (2002); Jua et al, *Org. Lett.*, 6:861 (2004); James et al., *Nature*, 374:345 (1995)). In $CH_2Cl_2$ solution containing 2% of DME, the fluorescence intensity of (S)-4 (0.10 mM) was increased 3.1 fold upon treatment of (S)-mandelic acid (5.0 mM), but only 1.9 fold for (R)-mandelic acid (5.0 mM). The net fluorescence intensity increase of (S)-4 by (S)-mandelic acid was 2.33 times that by (R)-mandelic acid. When (S)-4 (0.10 mM) was treated with mandelic acid in the concentration range of 5.0 mM to 20 mM, the fluorescence enhancement of the open complex exhibits a Benesi-Hildebrand type relationship (Benesi and Hildebrand, *J. Am. Chem. Soc.*, 71:2703 (1949)). Thus, the association constant of (S)-4+(S)-mandelic acid was found to be 764 NT, while that of (S)-4 and (R)-mandelic acid was 367 $M^{-1}$. This indicates that the complex (S)-4+(S)-mandelic acid is more stable than the (S)-4+(R)-mandelic acid by approximately 0.43 kcal/mol(ΔΔG).

Analyte Detection Via Catalytic Activity

The synthesis of the hemi-labile ligand and corresponding coordination complex outlined below can be used to synthesize other hemi-labile ligands and coordination complexes by variation of the starting materials, such as using a different diamine (e.g., 1,1'-diamino-naphthalene) or by coupling different aldehydes to the diamine. The appropriate choice of starting diamine or intermediate aldehyde will be readily apparent to one of skill in the art in the art in view of the examples set forth below.

3-tert-butyl-5-[4'-(2-diphenylphosphinoethanesulfanyl) phenyl]salicylaldehyde and (R,R)-(–)-1,2-cyclohexanediamino-N-(3,5-di-t-butylsalicylidene) hydrochloride were prepared via published procedures (Gianneschi et al, *J. Am. Chem. Soc.*, 125:10508 (2003) and Campbell et al., *Tetrahedron Lett.*, 42:1221 (2001)). Rhodium (I) norbornidene chloride dimer $[Rh(NBD)Cl]_2$ was purchased from Strem Chemicals (Newbury, Mass.) and used as received.

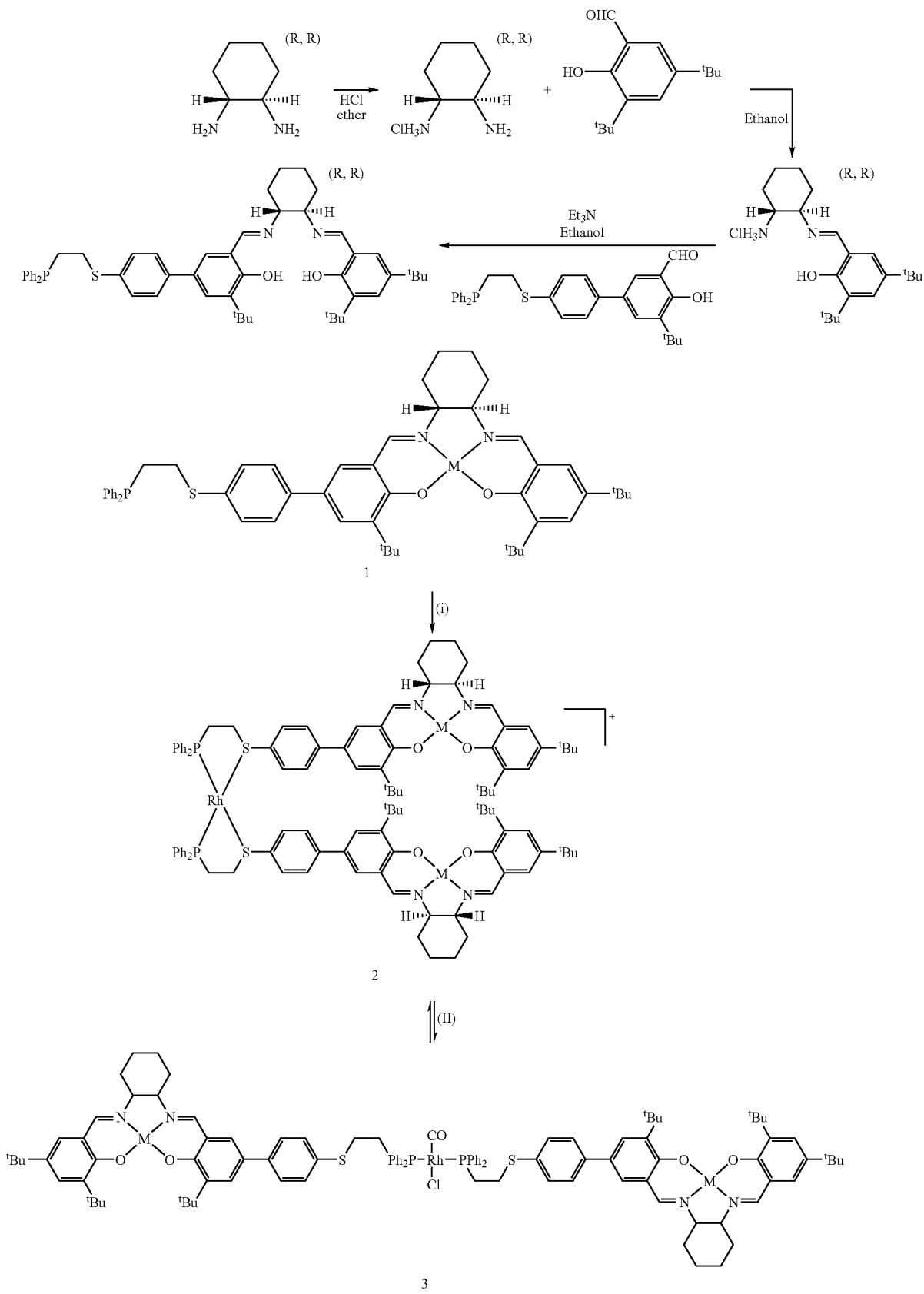

(R,R)-1,2-cyclohexanediamino-N-(3,5-di-t-butylsalicylidene)-N'-3-t-butyl-5-[4'-(2-diphenylphosphinoethanesulfanyl)phenyl]salicylidene. ($H_2L$) (R,R)-1,2-cyclohexanediamino-N-(3,5-di-t-butylsalicylidene)hydrochloride (0.74 g, 2.0 mmol) was placed in a Schlenk flask with triethylamine (0.28 mL, 2 mmol) and ethanol (5 mL) and stirred for 5 minutes (min) at which time 3-t-butyl-5-[4'-(2-diphenylphosphinoethanesulfanyl)phenyl]salicylaldehyde (1.0 g, 2.0 mmol) in $CH_2Cl_2$/ethanol (10 mL, 1:1) was added to the solution. The resulting yellow solution was stirred for 18 h before the solvent was removed in vacuo. The resulting yellow microcrystalline powder was purified by silica gel chromatography (1:1 $CH_2Cl_2$:hexanes). Yield 1.4 g (85%). $^1H$ NMR ($CDCl_3$): δ 14.02 (s, 1H, OH), 13.69 (s, 1H, OH), 8.33 (s, 1H, N=CH), 8.29 (s, 1H, N=CH), 7.43-6.96 (m, 18H, aromatic), 3.33 (m, 2H, cyclohexyl), 2.95 (m, 2H, $H_2C$—P), 2.36 (m, 2H, $H_2C$—S), 1.88 (m, 8H, cyclohexyl), 1.45 (s, 9H, $C(CH_3)_3$), 1.40 (s, 9H, $C(CH_3)_3$), 1.21 (s, 9H, $C(CH_3)_3$). $^{13}C\{^1H\}$ NMR ($CDCl_3$): δ 166.2, 165.7, 160.3, 158.1, 140.2, 139.4, 137.7 (d, $J_{P-C}$=5.7 Hz), 136.6, 133.9, 133.1, 132.8, 130.1, 129.0, 128.8 (d, $J_{P-C}$=6.3 Hz), 128.3, 127.3, 127.1, 126.2, 118.9, 118.0, 72.6, 38.2, 34.9, 33.4, 33.3, 31.8, 31.6, 31.5, 30.6 (d, $J_{P-C}$=21.9 Hz), 29.6, 29.5, 28.6 (d, $J_{P-C}$=14.9 Hz), 25.5, 24.5, 22.9. $^{31}P\{^1H\}$ NMR ($CDCl_3$): δ −16.0. High resolution EIMS (m/z): Calcd. for $C_{52}H_{63}O_2N_2SP$: 810.4342. Found: 810.4359. Anal. Calcd. for $C_{52}H_{63}O_2N_2SP$: C, 77.00; H, 7.83; N, 3.16. Found: C, 76.87; H, 7.56; N, 3.16.

Formation of Chromium Complex (1, structure above, M=CrCl). $H_2L$ (prepared above, 0.60 g, 0.74 mmol), chromium (II) chloride (0.18 g, 1.5 mmol), and tetrahydrofuran (THF, 20 mL) were combined in a small vial in an inert atmosphere glovebox and the resulting brown solution was stirred under a static nitrogen atmosphere for 3 h, then opened to air for a further 3 h. The solvent was removed in vacuo. The crude brown solid was dissolved in $CH_2Cl_2$, washed with saturated ammonium chloride (aq) and brine, and the organic layer was dried over sodium sulfate. Vacuum removal of the solvent and subsequent recrystallization from $CH_2Cl_2$/ether yielded a brown microcrystalline solid. Yield 0.50 g (75%). $^{31}P\{^1H\}$ NMR ($CD_2Cl_2$): δ −15.6 (broad s). EIMS (m/z): Calcd for [$C_{52}H_{61}O_2N_2PCrCl$]: 895.3. Found: 895.2. Anal. Calcd for $C_{52}H_{61}O_2N_2SPCrCl·CH_2Cl_2$: C, 64.95; H, 6.48; N, 2.86. Found: C, 65.18; H, 6.59; N, 3.10.

Formation of zinc complex (1, structure above, M=Zn). $H_2L$ (prepared above, 0.14 g, 0.17 mmol) was dissolved in THF (3 mL). To this solution diethyl zinc (0.023 g, 0.19 mmol) in THF (2 mL) was added. The resulting yellow solution was stirred for 22 h. The solvent was removed in vacuo. The crude yellow solid was; recrystallized from $CH_2Cl_2$/hexanes to, yield a microcrystalline solid. Yield 0.14 g (90%). $^1H$ NMR ($CD_2Cl_2$): δ 8.45 (s, 1H, N=CH), 8.39 (s, 1H, N=CH), 7.58-7.28 (m, 18H, aromatic), 3.15 (m, 2H, cyclohexyl), 2.98 (m, 2H, $H_2C$—P), 2.44 (m, 2H, $H_2C$—S), 1.99 (m, 8H, cyclohexyl), 1.50 (s, 9H, $C(CH_3)_3$), 1.49 (s, 9H, $C(CH_3)_3$), 1.34 (s, 9H, $C(CH_3)_3$). $^{31}P\{^1H\}$ NMR ($CD_2Cl_2$): δ −16.3. EIMS (m/z): Calcd for [$C_{52}H_{61}O_2N_2SPZn$]: 872.35. Found: 872.35. Anal calcd for $C_{52}H_{61}O_2N_2SPZn$: C, 71.53; H, 7.05; N, 3.21. Found: C, 71.43; H, 6.97; N, 2.98.

Formation of rhodium/chromium complex (2, structure above, M=CrCl). A small vial was charged with [Rh(NBD)Cl]$_2$ (0.052 g, 0.11 mmol), silver tetrafluoroborate (0.044 g, 0.22 mmol), and $CH_2Cl_2$ (2 mL). This reaction was stirred for 2 h then filtered dropwise through Celite into a Schlenk flask. The resulting red solution the was diluted with $CH_2Cl_2$ (10 mL) to give a light red/orange "Rh" solution. Compound 1 (from above, 0.40 g, 0.45 mmol) in $CH_2Cl_2$ (10 mL) was added to the "Rh" solution and allowed to stir for 22 h. The solvent was removed in vacuo to yield a brown microcrystalline solid. This solid then was dissolved in a minimal amount of $CH_2Cl_2$ and filtered through Celite. The brown-solution then was recrystallized from $CH_2Cl_2$/hexanes. Yield 0.40 g (90%). $^{31}P\{^1H\}$ NMR ($CD_2Cl_2$): δ 67.7 (br). ESMS (m/z): Calcd. for [$C_{104}H_{122}O_4N_4S_2P_2RhCr_2Cl_2$]+: 1896.1. Found: 1896.2. Anal. Calcd. for ($C_{104}H_{122}O_4N_4S_2P_2RhCr_2Cl_2$ $BF_4$)·½$CH_2Cl_2$: C, 61.97; H, 6.12; N, 2.77. Found: C, 62.13; H, 6.18; N, 2.71.

Formation of rhodium/zinc complex (2, structure above, M=Zn). A small vial was charged with [Rh(NBD)Cl]$_2$ (0.015 g, 0.03 mmol), silver tetrafluoroborate (0.012 g, 0.06 mmol), and $CH_2Cl_2$ (2 mL). This reaction was stirred for 2 h, then filtered dropwise through Celite into a Schlenk flask. The resulting red solution then was diluted with $CH_2Cl_2$ (10 mL) to give a light red/orange "Rh" solution. Compound 2 (from above, 0.11 g, 0.13 mmol) in $CH_2Cl_2$ (10 mL) was added to the "Rh" solution and stirred for 22 h. The solvent was removed in vacuo to yield a yellow microcrystalline solid which was recrystallized from $CH_2Cl_2$/hexanes. Yield 0.12 g (95%). $^1H$ NMR ($CD_2Cl_2$): δ 8.84 (br, 4H, N=CH), 7.74-7.23 (m, 36H, aromatic), 3.71 (m, 4H, cyclohexyl), 2.81 (m, 4H, $H_2C$—P), 2.66 (m, 4H, $H_2C$—S), 2.16 (m, 16H, cyclohexyl), 1.50 (s, 18H, $C(CH_3)_3$), 1.47 (s, 18H, $C(CH_3)_3$), 1.34 (s, 18H, $C(CH_3)_3$). $^{31}P\{^1H\}$ NMR ($CD_2Cl_2$): δ 66.3 (d, $J_{P-Rh}$=162 Hz). ESMS (m/z): Calcd for [$C_{104}H_{122}O_4N_4S_2P_2RhZn_2$]$^+$: 1851.9. Found: 1851.7. Anal. Calcd for ($C_{104}H_{122}O_4N_4S_2P_2RhZn_2BF_4$)·$CH_2Cl_2$: C, 62.32; H, 6.18; N, 2.77. Found: C, 62.41; H, 5.97; N, 2.66.

Synthesis of the "open" macrocycles (3, structure above, M=Zn or CrCl). Compound 2 (M=Zn or M=CrCl) was placed in NMR tubes in either benzonitrile, THF, or $CH_2Cl_2$ in the presence of 1 equiv bis(triphenylphosphoranylidene)ammonium chloride (PPNCl). Benzyltriethylammonium chloride also can be used as efficiently. CO (1 atm) then was bubbled through the solutions for 30 seconds. Yields of complex 3 (M=Zn or M=CrCl) were quantative as determined by $^{31}P\{^1H\}$ NMR spectroscopy. The liability of the Cl and CO ligands precluded elemental analysis and determination of the mass of the parent ion by mass spectrometry.

3, M=CrCl: $^{31}P\{^1H\}$ NMR ($CD_2Cl_2$): δ 25.4 (br), 21.2 (s, PPN). FTIR: $v_{CO}$=1976 cm$^{-1}$. ESMS (m/z): Calcd for [$C_{104}H_{122}O_4N_4S_2P_2RhCr_2Cl_2$]$^+$: 1896.1. Found: 1896.0.

3, M=Zn: $^1H$ NMR ($CD_2Cl_2$): δ 8.50 (s, 2H, N=CH), 8.41 (s, 2H, N=CH), 7.72-7.31 (m, 36H, aromatic), 3.65 (m, 4H, cyclohexyl), 3.01 (m, 4H, $H_2C$—P), 2.45 (m, 4H, $H_2C$—S), 1.98 (m, 16H, cyclohexyl), 1.51 (s, 18H, $C(CH_3)_3$), 1.47 (s, 18H, $C(CH_3)_3$), 1.31 (s, 18H, $C(CH_3)_3$). $^{31}P\{^1H\}$ NMR ($CD_2Cl_2$): δ 23.5 (d, $J_{P-Rh}$=123 Hz), 21.2 (s, PPN). FTIR: $v_{CO}$=1978 cm$^{-1}$. ESMS (m/z): Calcd for [$C_{104}H_{122}O_4N_4S_2P_2RhZn_2$]$^+$: 1851.9. Found: 1851.7.

Catalytic Experiments

Product formation was monitored by GC on a Selco β-dex 120 chiral column relative to 1,2,4,5-tetramethylbenzene. All reactions were performed at room temperature. In the examples below "solvent" refers to either THF or benzonitrile.

"Closed" catalyst experiment—no allosteric effectors: Complex 2 (above, M=CrCl) (0.01 g, 7.5×10$^{-2}$ mmol), cyclohexene oxide (0.6 mL, 6.1 mmol), and solvent (0.5 mL) were added to a 10 mL Schlenk flask and stirred for 5 min. After this time, TMSN$_3$ (0.3 mL, 2.3 mmol) was added to the solution. At various times (typically 0.5 h apart), a 0.05 mL aliquot was taken from the solution and added to diethyl ether (1 mL). This aliquot then was passed down a (3×0.5) cm plug of silica gel and eluted with diethyl ether (5 mL). Samples were taken for GC from the eluent.

"Open" catalyst experiments—allosteric effectors present. Complex 2 (above, M=CrCl) (0.01 g, 5.1×10$^{-3}$ mmol), PPNCl (2.9 mg, 5.1×10$^{-3}$ mmol) and solvent (0.1 mL) were added to a 10 mL Schlenk flask. This solution then was purged with CO for 30 seconds. 1,2,4,5-tetramethylbenzene (0.01 g, 7.5×10$^{-2}$ mmol), cyclohexene oxide (0.6 mL, 6.1 mmol) and solvent (0.4 mL) were added to the flask and stirred for 5 min. TMSN$_3$ (0.3 mL, 2.3 mmol) was then added to the solution. At various time points (typically 0.5 h apart), a 0.05 mL aliquot was taken from the solution and added to diethyl ether (1 mL). This aliquot then was passed down a (3×0.5) cm plug of silica gel and eluted with diethyl ether (5 mL). Samples were taken for GC from the eluent.

In situ Cycling Experiment (FIG. 2): Complex 2 (above, M=CrCl) (0.01 g, 5.1×10$^{-3}$ mmol), PPNCl (2.9 mg, 5.1×10$^{-3}$ mmol), 1,2,4,5-tetramethylbenzene (0.01 g, 7.5×10$^{-2}$ mmol), cyclohexeneoxide (0.6 mL, 6.1 mmol), and benzonitrile (0.5 mL) were added to a 10 mL Schlenk flask and stirred for 5 min. After this time, TMSN$_3$ (0.3 mL, 2.3 mmol) was added to the solution. At various time points (typically 0.5 h apart), a 0.05 mL aliquot was taken from the solution and added to diethyl ether (1 mL). This aliquot then was passed down a (3×0.5) cm plug of silica gel and eluted with diethyl ether (5 mL). Samples were taken for the GC from the eluent. At 110 min, the solution was exposed to CO using a syringe containing 20 mL of CO. At 240 min, the solution was purged with 30 mL of nitrogen using a gas-tight syringe. The reaction progress was monitored using GC. The reverse of this experiment was performed wherein the starting solution was exposed to CO prior to TMSN$_3$ addition and subsequently purged with N$_2$ at 110 min, and then again with CO at 240 min. FIG. 2, right, shows the amount of product produced under both of these experimental conditions.

Figure 4:
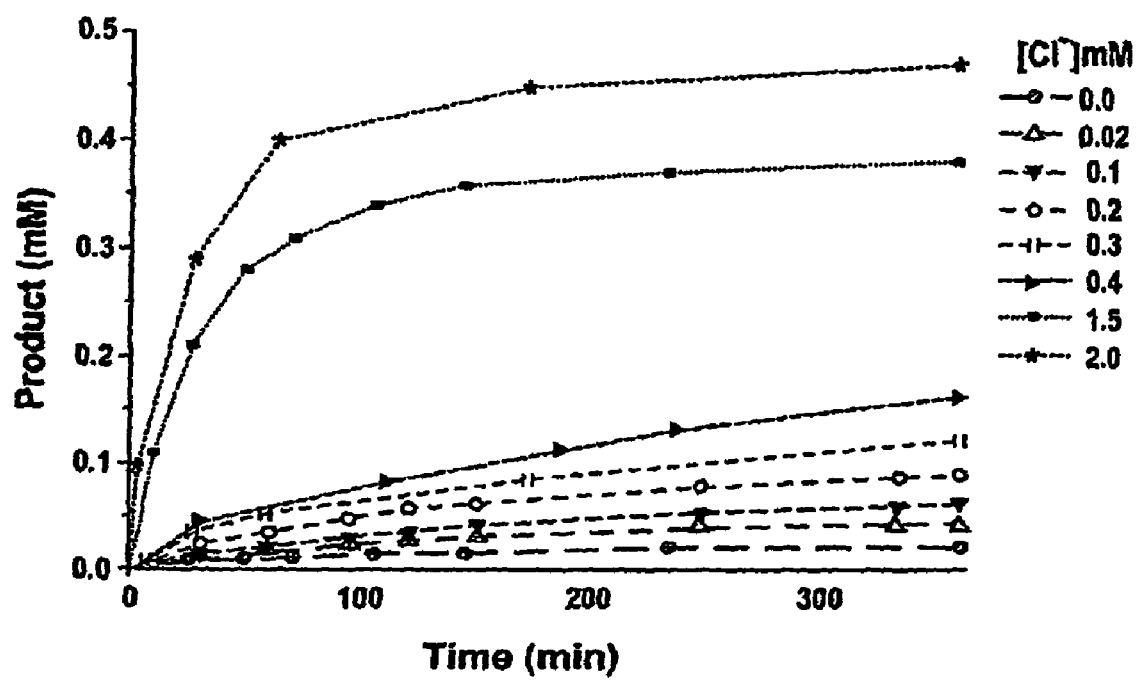
FIG. 4 shows the amount of product formed with the catalyst of FIG. 1 in the presence of various concentrations of chloride ion.

In another example, the formation of 4-acetoxymethylpyridine was monitored by GC relative to an internal standard (biphenyl) and quantified using a previously established calibration curve. All reactions were performed at room temperature in CH$_2$Cl$_2$. Complex 1 (FIG. 1, top complex, 1 mM), biphenyl (1.5 mM), pyridyl carbinol (1 mM), acetic anhydride (1 mM), and appropriate amounts of benzyltriethylammonium chloride (see FIG. 4) were added to a 10 mL Schlenk flask, followed by introduction of CO (1 atm). The total volume of the reactions was 2.5 mL CH$_2$Cl$_2$. At various times (typically 0.5 h apart), a 0.1 mL aliquot was taken from the solution and added to diethyl ether (2 mL). This aliquot then was passed down a plug of Celite (3 cm×0.5 cm). The resulting samples were used for GC analysis. The GC settings were as follows: initial time—0 min, initial temperature—65° C., final temperature—135° C., rate—5° C./min, final time—14 min.

What is claimed is:

1. A coordination complex having a structural formula

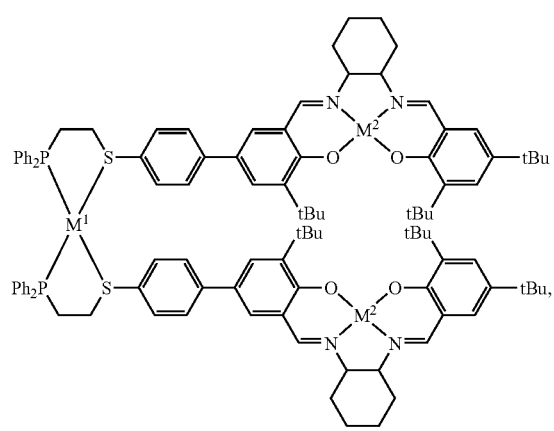

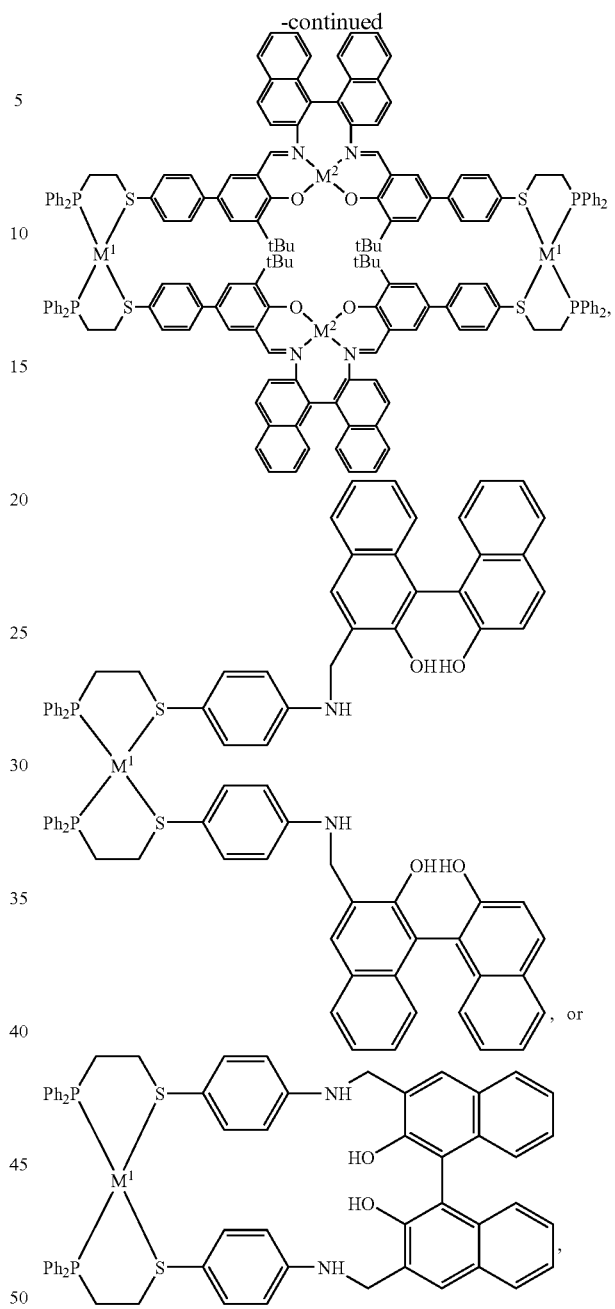

wherein Ph is phenyl, tBu is tert-butyl, M$^1$ and M$^2$ are different and independently selected from the group consisting of copper, zinc, nickel, cobalt, manganese, chromium, vanadium, titanium, scandium, yttrium, zirconium, niobium, molybdenum, technetium, ruthenium, rhodium, palladium, silver, cadmium, lanthanum, hafnium, tantalum, tungsten, rhenium, osmium, iridium, platinum, gold, tin, cerium, aluminum, magnesium, calcium, strontium, barium, praseodymium, neodymium, promethium, samarium, europium, gadolinium, terbium, dysprosium, holmium, erbium, thulium, ytterbium, and lutetium.

2. The coordination complex of claim 1 wherein M$^2$ is selected from the group consisting of copper, zinc, and chromium.

3. The coordination complex of claim 1 wherein $M^1$ is rhodium.

4. A hemi-labile ligand have the formula

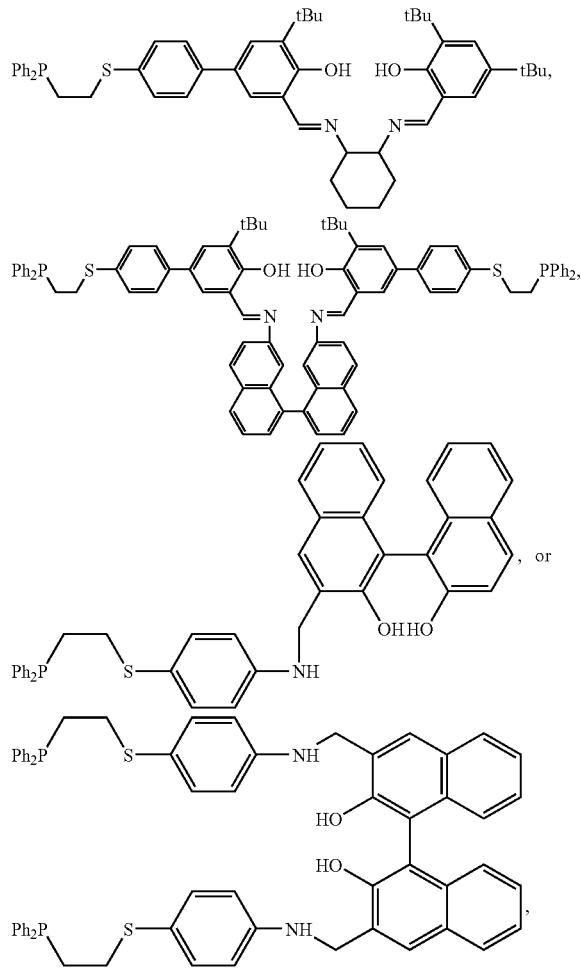

wherein Ph is phenyl and tBu is tert-butyl.

5. A method of detecting an analyte comprising the steps of:
   a) providing a coordination complex having a first structural conformation and at least one metal center and at least one hemi-labile ligand, said hemi-labile ligand having at least one weakly associating coordinating atom and at least one strongly associating coordination atom, said weakly associating atom capable of being displaced from the metal center by a second ligand;
   b) contacting the coordination complex with an allosteric effector, wherein the allosteric effector coordinates to the coordination complex and causes at least one hemi-labile ligand to rearrange its coordination to the metal center to produce a second conformation of the coordination complex;
   c) contacting the second conformation of the coordination complex produced in step (b) with a test sample to produce a mixture; and
   d) monitoring the mixture resulting from step (c) to detect to the presence of the analyte in the test sample.

6. The method of claim 5 wherein the metal center is selected from the group consisting of copper, zinc, nickel, cobalt, manganese, chromium, vanadium, titanium, scandium, yttrium, zirconium, niobium, molybdenum, technetium, ruthenium, rhodium, palladium, silver, cadmium, lanthanum, hafnium, tantalum, tungsten, rhenium, osmium, iridium, platinum, gold, tin, cerium, aluminum, magnesium, calcium, strontium, barium, praseodymium, neodymium, promethium, samarium, europium, gadolinium, terbium, dysprosium, holmium, erbium, thulium, ytterbium, and lutetium.

7. The method of claim 5 wherein the coordination atoms of the hemi-labile ligand are selected from the group consisting of phosphorus, sulfur, nitrogen and oxygen.

8. The method of claim 5 wherein the coordination atoms of the hemi-labile ligand comprise a phosphorus coordinating atom and a sulfur coordinating atom.

9. The method of claim 8 wherein the hemi-labile ligand is a 2-diphenylphosphanyl-ethanethiol ether.

10. The method of claim 5 wherein the means for monitoring is selected from the group consisting of liquid chromatography, gas chromatography, fluorescence, mass spectrometry, infrared spectroscopy, raman spectroscopy, and nuclear magnetic resonance.

11. The method of claim 5 wherein the coordination complex is chiral.

12. The method of claim 11 wherein the analyte is chiral.

13. The method of claim 12 further comprising separating the chiral analyte from a racemic mixture.

14. A method of detecting an analyte comprising the steps of:
   a) providing a coordination complex having at least one metal center and at least one hemi-labile ligand, said hemi-labile ligand having at least one weakly associating coordinating atom and at least one strongly associating coordination atom, said weakly associating atom capable of being displaced from the metal center by a second ligand;
   b) contacting the coordination complex with a test sample, wherein the coordination complex rearranges at least one hemi-labile ligand in the presence of the analyte and activates the coordination complex as a catalyst for a reaction to produce a reaction solution;
   c) monitoring for production of a product of the reaction or consumption of a substrate of the reaction in the reaction solution to detect the presence or absence of the analyte in the test sample.

15. The method of claim 14 wherein the coordination complex comprises a metal center selected from the group consisting of copper, zinc, nickel, cobalt, manganese, chromium, vanadium, titanium, scandium, yttrium, zirconium, niobium, molybdenum, technetium, ruthenium, rhodium, palladium, silver, cadmium, lanthanum, hafnium, tantalum, tungsten, rhenium, osmium, iridium, platinum, gold, tin, cerium, aluminum, magnesium, calcium, strontium, barium, praseodymium, neodymium, promethium, samarium, europium, gadolinium, terbium, dysprosium, holmium, erbium, thulium, ytterbium, and lutetium.

16. The method of claim 15 wherein the metal center is selected from the group consisting of rhodium, chromium, copper, and zinc.

17. The method of claim 14 wherein the coordination atoms of the hemi-labile ligand are selected from the group consisting of phosphorus, sulfur, nitrogen and oxygen.

18. The method of claim 17 wherein the coordination atoms of the hemi-labile ligand comprise a phosphorus coordinating atom and a sulfur coordinating atom.

19. The method of claim 18 wherein the hemi-labile ligand is a 2-diphenylphosphanyl-ethanethiol ether.

20. The method of claim 14 wherein the coordination complex is chiral.

21. The method of claim 20 wherein the analyte is chiral.

22. The method of claim 21 further comprising separating one enantiomer of the analyte from the other enantiomer.

23. The method of claim 14 wherein a sensor molecule is the means of monitoring the production of the product or consumption of the substrate of the reaction.

24. The method of claim 23 wherein the sensor molecule changes fluorescence or color in the presence of the product of the catalytic reaction.

25. The method of claim 14 wherein the production of the product or consumption of the substrate alters the fluorescence or the color of the reaction solution.

* * * * *

UNITED STATES PATENT AND TRADEMARK OFFICE
CERTIFICATE OF CORRECTION

PATENT NO. : 7,754,907 B2
APPLICATION NO. : 11/658606
DATED : July 13, 2010
INVENTOR(S) : Chad A. Mirkin et al.

It is certified that error appears in the above-identified patent and that said Letters Patent is hereby corrected as shown below:

Col. 1 line 15 should read
    This invention was made with government support under Grant No. EEC 0118025 awarded by the National Science Foundation and under Grant No. F49620-00-1-0283 awarded by the Air Force Office of Scientific Research. The government has certain rights in the invention.

Signed and Sealed this

Fifth Day of October, 2010

David J. Kappos
*Director of the United States Patent and Trademark Office*